(12) United States Patent
Okamoto et al.

(10) Patent No.: US 9,499,576 B2
(45) Date of Patent: *Nov. 22, 2016

(54) COMPOUND, NUCLEIC, ACID, METHOD FOR PRODUCING NUCLEIC ACID, AND KIT FOR PRODUCING NUCLEIC ACID

(75) Inventors: Akimitsu Okamoto, Wako (JP); Shuji Ikeda, Wako (JP)

(73) Assignee: RIKEN, Wako-shi, Saitama (JP)

( * ) Notice: Subject to any disclaimer, the term of this patent is extended or adjusted under 35 U.S.C. 154(b) by 300 days.

This patent is subject to a terminal disclaimer.

(21) Appl. No.: 13/997,700

(22) PCT Filed: Dec. 28, 2011

(86) PCT No.: PCT/JP2011/080386
§ 371 (c)(1),
(2), (4) Date: Jun. 25, 2013

(87) PCT Pub. No.: WO2012/091091
PCT Pub. Date: Jul. 5, 2012

(65) Prior Publication Data
US 2013/0289263 A1     Oct. 31, 2013

(30) Foreign Application Priority Data
Dec. 28, 2010 (JP) ................................ 2010-293074

(51) Int. Cl.
| | | |
|---|---|---|
| C07H 21/04 | (2006.01) | |
| C07H 21/00 | (2006.01) | |
| C07H 19/10 | (2006.01) | |
| C07H 19/048 | (2006.01) | |
| C07H 19/073 | (2006.01) | |

(52) U.S. Cl.
CPC ............ *C07H 19/10* (2013.01); *C07H 19/073* (2013.01); *C07H 21/04* (2013.01)

(58) Field of Classification Search
CPC ................. C07H 19/073; C07H 19/10; C07H 21/04
See application file for complete search history.

(56) References Cited

U.S. PATENT DOCUMENTS

| | | |
|---|---|---|
| 5,656,449 A | 8/1997 | Yue |
| 8,067,162 B2 | 11/2011 | Hayashizaki et al. |
| 8,383,792 B2 | 2/2013 | Okamoto et al. |
| 2008/0227104 A1 | 9/2008 | Hayashizaki et al. |
| 2010/0092971 A1 | 4/2010 | Okamoto et al. |
| 2010/0093992 A1 | 4/2010 | Cherkasov et al. |

FOREIGN PATENT DOCUMENTS

WO    2008/111485 A1    9/2008

OTHER PUBLICATIONS

International Search Report (English translation), PCT/JP2011/080386, mailed Apr. 3, 2012.
Ikeda, Shuji, et al., "pH-dependent fluorescence of uncharged benzothiazole-based dyes binding to DNA," Photochem. Photobiol. Sci., vol. 6, 2007, pp. 1197-1201.
Okamoto, Akimitsu, "Excitonic Interaction: Another Photophysical Process for Fluorescence-Controlled Nucleic Acid Sensing," The Chemical Record, vol. 10, 2010, pp. 188-196.
Okamoto, Akimitsu, et al., "A nucleic acid probe labeled with desmethyl thiazole orange: a new type of hybridization-sensitive fluorescent oligonucleotide for live-cell RNA imaging," Organic & Biomolecular Chemistry, vol. 11, 2013, pp. 362-371.

*Primary Examiner* — Lawrence E Crane
(74) *Attorney, Agent, or Firm* — Casimir Jones, S.C.

(57) ABSTRACT

The present invention relates to a compound represented by Formulas 1, 2 or 3 as described herein, and a nucleic acid each of which contains a dye exhibiting an exciton effect, a method of producing such a nucleic acid by using the compound, and a kit for producing the nucleic acid.

11 Claims, 3 Drawing Sheets

SEQUENCE LISTING

```
<160> NUMBER OF SEQ ID NOS: 3

<210> SEQ ID NO 1
<211> LENGTH: 13
<212> TYPE: DNA
<213> ORGANISM: Artificial sequence
<220> FEATURE:
<223> OTHER INFORMATION: Artificial DNA probe
<220> FEATURE:
<221> NAME/KEY: misc_feature
<222> LOCATION: (7)..(7)
<223> OTHER INFORMATION: n is an artificial nucleoside of the present
      invention

<400> SEQUENCE: 1
tttttntttt ttt                                                        13

<210> SEQ ID NO 2
<211> LENGTH: 13
<212> TYPE: DNA
<213> ORGANISM: Artificial sequence
<220> FEATURE:
<223> OTHER INFORMATION: complementary strand for the Artificial DNA
      probe

<400> SEQUENCE: 2
aaaaaaaaaa aaa                                                        13

<210> SEQ ID NO 3
<211> LENGTH: 13
<212> TYPE: DNA
<213> ORGANISM: Artificial sequence
<220> FEATURE:
<223> OTHER INFORMATION: Artificial DNA probe
<220> FEATURE:
<221> NAME/KEY: misc_feature
<222> LOCATION: (7)..(7)
<223> OTHER INFORMATION: n is an artificial nucleoside of the present
      invention
```

```
<400> SEQUENCE: 3
taccagncac cat                                                    13
```

COMPOUND, NUCLEIC, ACID, METHOD FOR PRODUCING NUCLEIC ACID, AND KIT FOR PRODUCING NUCLEIC ACID

CROSS REFERENCE TO RELATED APPLICATIONS

The present application is a Section 371 U.S. national stage entry of pending International Patent Application No. PCT/JP2011/080386, International Filing Date Dec. 28, 2011, which claims the benefit of Japanese Patent Application No. 2010-293074, filed Dec. 28, 2010, the contents of which are incorporated by reference in their entireties.

TECHNICAL FIELD

The present invention relates to a compound and a nucleic acid each of which contains a dye exhibiting an exciton effect, a method of producing such a nucleic acid by using the compound, and a kit for producing the nucleic acid.

BACKGROUND ART

One of methods of detecting a nucleic acid is a method with use of a probe whose fluorescence emission is controllable by "exciton effect (exciton coupling effect)", as to whether or not to emit fluorescence.

As one example of a probe for detecting a nucleic acid by using the exciton effect as described above, Patent Literature 1 discloses a probe which contains a compound having a structure derived from mononucleoside or mononucleotide. The compound is, for example, attached to two fluorescent molecules. The probe emits extremely weak fluorescence while not being bound to DNA etc. because a structure of the probe is distorted and an exciton coupling causes quenching. The probe, however, emits strong fluorescence when the probe is hybridized with DNA or RNA because such distortion of the structure is solved and the structure is fixed.

CITATION LIST

Patent Literature

Patent Literature 1
Pamphlet of International Publication WO 2008/111485 (Publication date: Sep. 18, 2008)

SUMMARY OF INVENTION

Technical Problem

One of known methods of producing a nucleic acid probe is a method of synthesizing a nucleic acid probe by a phosphoramidite method with use of a phosphoramidite form of nucleoside (see Patent Literature 1). As a method of producing a nucleic acid probe for detecting a nucleic acid by using an exciton effect, Patent Literature 1 discloses a method in which a phosphoramidite form of nucleoside having no fluorescent molecule is synthesized, a DNA oligomer is formed with use of the phosphoramidite form of nucleoside thus synthesized, and then fluorescent molecules are introduced into the DNA oligomer.

The above method, however, needs two synthesizing steps, i.e., a synthesizing step of a DNA oligomer and a synthesizing step of synthesizing the DNA oligomer with fluorescent molecules to introduce the fluorescent molecules, and, in addition, needs purifying steps for the respective synthesizing steps. If an introduction efficiency of fluorescent molecules is not 100%, there might be produced a defective nucleic acid probe in which only one fluorescent molecule is introduced.

Because fluorescent molecules are introduced after a DNA oligomer is synthesized in conventional methods, it is difficult to introduce several different kinds of dyes (fluorescent molecules) into different positions of the DNA oligomer.

The present invention has been made in view of problems that conventional techniques have, and an object of the present invention is to provide a compound which makes it easy to produce a nucleic acid which contains a dye exhibiting the exciton effect, and also to provide the nucleic acid, a method of producing the nucleic acid, and a kit for producing the nucleic acid.

Solution to Problem

The inventors of the present invention have diligently studied to attain the object. As a result, the inventors achieved the present invention by finding the following points.

In order to easily produce a nucleic acid which contains a dye exhibiting the exciton effect, the inventors of the present invention firstly focused on a method of synthesizing an oligo-nucleic acid with use of a phosphoramidite compound containing a dye. As the dye exhibiting the exciton effect, there has been conventionally used in general a molecule having an electric charge (positive charge) which is considered to be relevant to exhibition of the exciton effect. The inventors of the present invention tried to synthesize a nucleic acid by using such a conventional molecule having a dye, however, in some cases, a synthesizing efficiency was not enough.

In a case where the molecule having the electric charge was used as a dye exhibiting the exciton effect, a precursor (OH body) of an amidite form, into which the dye was incorporated, could be produced, however, an amidite form could not be efficiently synthesized from the precursor thus produced.

In view of the circumstances, the inventors of the present invention tried to synthesize a nucleic acid by using a phosphoramidite compound containing a dye and an uncharged dye, and found that the synthesis of the nucleic acid can be performed with an enough synthesizing efficiency. That is, the inventors of the present invention found that the phosphoramidite compound can be used as a nucleoside substrate to synthesize a nucleic acid. The inventors of the present invention further found that a nucleic acid which has been produced with use of the phosphoramidite compound exhibits the exciton effect.

That is, a compound of the present invention is represented by the following formulae (1), (2), or (3).

[Chem. 1]

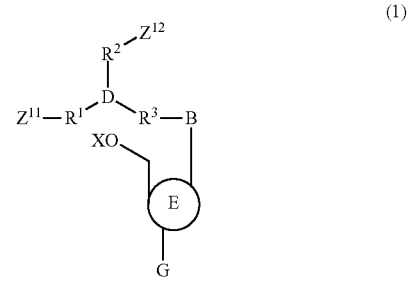

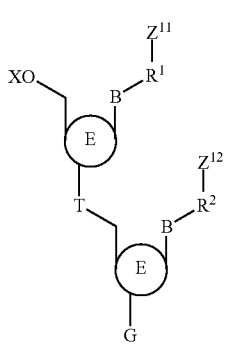

(2)

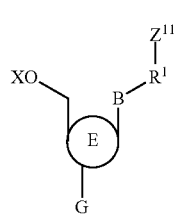

(3)

(where, in the above formulae (1), (2), and (3),

G is a phosphoramidite group represented by the following formula (33) or a hydroxyl group,

[Chem. 2]

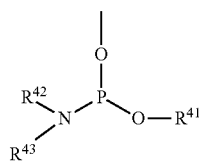

(33)

B is an atomic group having a basic skeleton,

E is an atomic group having a deoxyribose skeleton or a ribose skeleton, or a derivative of the atomic group, $Z^{11}$ and $Z^{12}$ are independently uncharged atomic groups each having a fluorescent property and exhibiting an exciton effect, and may be identical to or different from each other, X is a hydrogen atom, a protecting group for protecting a hydroxyl group, the protecting group being deprotectable by an acid, a phosphate group, a diphosphate group, or a triphosphate group, $R^{41}$ is a protecting group of a phosphate group, $R^{42}$ and $R^{43}$ are independently alkyl groups or aryl groups, $R^1$ and $R^2$ are independently linkers each having a main chain, and an atom forming the main chain optionally has a substituent, $R^3$ is a linker having a main chain, or is absent, and an atom forming the main chain optionally has a substituent, D is $CR^{11}$, N, P, P=O, B (boron atom), $SiR^{11}$, or absent, and $R^{11}$ is a hydrogen atom, an alkyl group, or an arbitrary substituent, D is directly attached to B in a case where $R^3$ does not exist and D exists, $R^1$ and $R^2$ are directly attached to $R^3$ in a case where $R^3$ exists and D does not exist, and $R^1$ and $R^2$ are directly attached to B in a case where both $R^3$ and D do not exist, and T is phosphate bridge, and wherein, in the phosphate bridge, one or more oxygen atoms are optionally substituted with one or more sulfur atoms.)

Further, the compound of the present invention is not particularly limited by the following specific examples, however, it is preferable that, in the above formulae (1) and (3), an atomic group represented by the following formula (1a) is an atomic group represented by the following formula (4) or (5); and, in the above formula (2), an atomic group represented by the following formula (2a) is an atomic group represented by the following formula (6) or (7).

[Chem. 3]

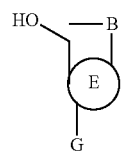

(1a)

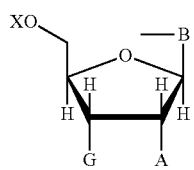

(4)

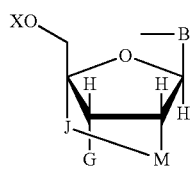

(5)

[Chem. 4]

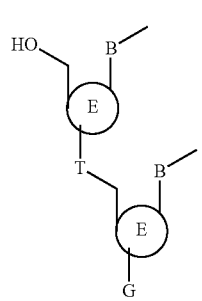

(2a)

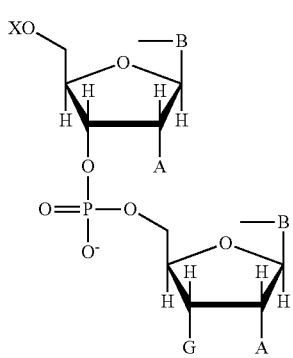

(6)

-continued (7)

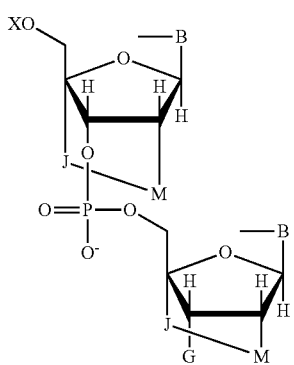

(where, in the above formulae (4) through (7),

A is a hydrogen atom, a hydroxyl group, an alkyl group, or an electron attracting group, and M and J are independently $CH_2$, NH, O, or S.)

Further, the compound of the present invention is not particularly limited by the following specific examples, however, it is preferable that main chains of $R^1$, $R^2$, and $R^3$ are independently constituted by two or more atoms.

Further, the compound of the present invention is not particularly limited by the following specific examples, however, is preferably represented the following formula (8), (9), (10), or (11).

[Chem. 5]

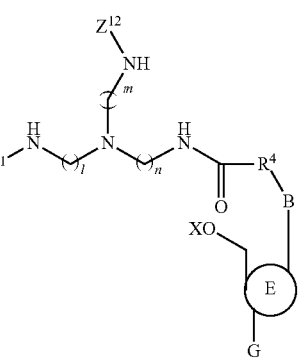

(8)

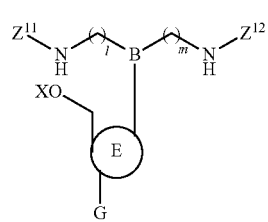

(9)

[Chem. 6]

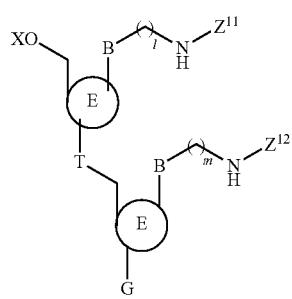

(10)

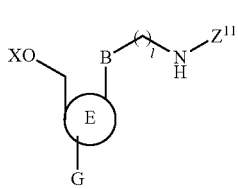

(11)

(where, in the above formulae (8), (9), (10), and (11), l, m, and n are independently positive integers, and $R^4$ is a single bond, a double bond, or a triple bond, or is absent.)

Further, the compound of the present invention is not particularly limited by the following specific examples, however, it is preferable that l, m, and n are 2, and $R^4$ is a double bond.

Further, the compound of the present invention is not particularly limited by the following specific examples, however, it is preferable that $Z^{11}$ and $Z^{12}$ are independently atomic groups represented by the following formula (12), (28), or (29).

[Chem. 7]

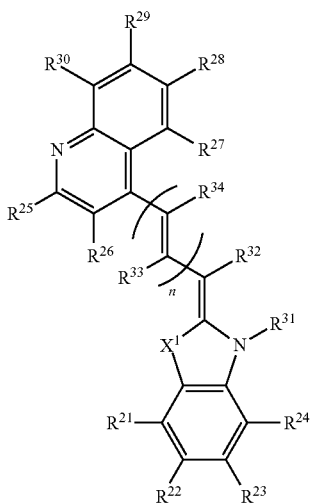

(12)

-continued

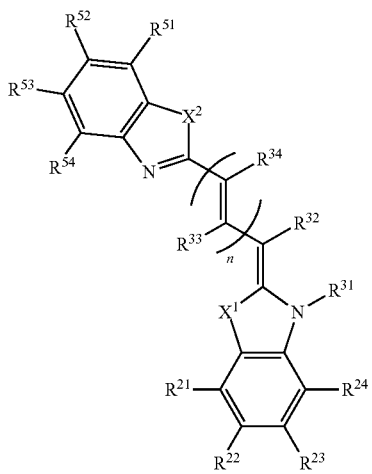
(28)

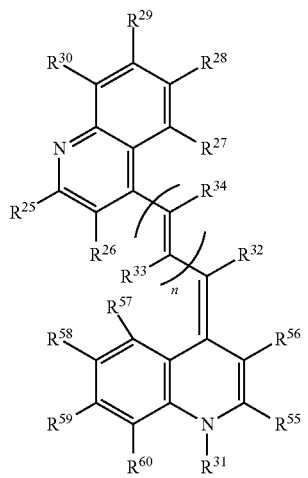
(29)

(where, in the above formulae (12), (28), and (29), $X^1$ and $X^2$ are independently O, S, Se, or Te, n is zero or a positive integer, $R^{21}$ to $R^{30}$, $R^{32}$ to $R^{34}$, $R^{51}$ to $R^{60}$ are independently hydrogen atoms, halogens, lower alkyl groups, lower alkoxy groups, nitro groups, or amino groups, and $R^{28}$ and $R^{29}$ are optionally attached to each other, and $R^{58}$ and $R^{59}$ are optionally attached to each other, $R^{31}$ is a linking group which is attached to $R^1$ or $R^2$ in the above formula (1), (2), or (3), or is a linking group which is attached to NH in the above formula (8), (9), (10), or (11), and in a case where n is an integer of 2 or more, $R^{33}$ and may be identical to or different from each other, and $R^{34}$ may be identical to or different from each other.)

Further, the compound of the present invention is not particularly limited by the following specific examples, however, it is preferable that $R^{31}$ be a polymethylene carbonyl group having two or more carbon atoms in the above formula (12), (28), and (29); and a carbonyl group portion of the polymethylene carbonyl group having two or more carbon atoms is attached to $R^1$ or $R^2$ in the above formula (1), (2), or (3), or is attached to NH in the above formula (8), (9), (10), or (11).

Further, the compound of the present invention is not particularly limited by the following specific examples, however, it is preferable that $R^{41}$ be a cyanoethyl group, both $R^{42}$ and $R^{43}$ are isopropyl groups.

A method of producing a nucleic acid in accordance with the present invention, includes carrying out a condensation reaction of a compound in any one of the above compounds and an oligonucleic acid, the compound being such that G is a phosphoramidite group represented by the above formula (33).

A nucleic acid of the present invention is an atomic group, represented by the following formula (25), (26), or (27), as a nucleotide portion.

[Chem. 8]

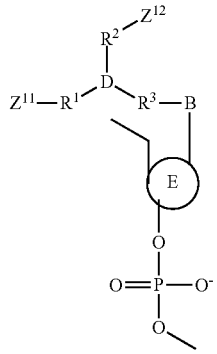
(25)

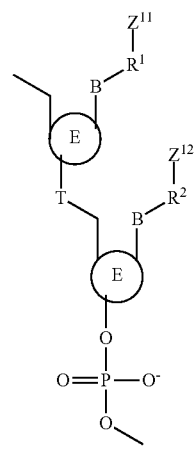
(26)

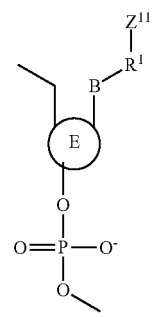
(27)

(where, in the above formulae (25), (26), and (27),

B is an atomic group having a basic skeleton,

E is an atomic group having a deoxyribose skeleton or a ribose skeleton, or a derivative of the atomic group, $Z^{11}$ and $Z^{12}$ are independently uncharged atomic groups each having a fluorescent property and exhibiting an exciton effect, and may be identical to or different from each other, $R^1$ and $R^2$ are independently linkers each having a main chain, and an atom forming the main chain optionally has a substituent, $R^3$ is a linker having a main chain, or is absent, and an atom forming the main chain optionally has a substituent, D is $CR^{11}$, N, P, P=O, B (boron atom), $SiR^{11}$, or absent, and $R^{11}$ is a hydrogen atom, an alkyl group, or an arbitrary substituent, D is directly attached to B in a case where $R^3$ does not exist and D exists, $R^1$ and $R^2$ are directly attached to $R^3$ in a case where $R^3$ exists and D does not exist, and $R^1$ and $R^2$ are directly attached to B in a case where both $R^3$ and D do not exist, and T is phosphate bridge, and wherein, in the phosphate bridge, one or more oxygen atoms are optionally substituted with one or more sulfur atoms).

Further, the nucleic acid of the present invention is not particularly limited, however, it is preferable to employ the above method of producing a nucleic acid.

A kit for producing the nucleic acid in accordance with the present invention contains any one of the above compounds.

Advantageous Effects of Invention

According to a compound of the present invention, it is possible to easily produce a nucleic acid probe which contains a dye exhibiting an exciton effect.

DESCRIPTION OF EMBODIMENTS

Figure 1:
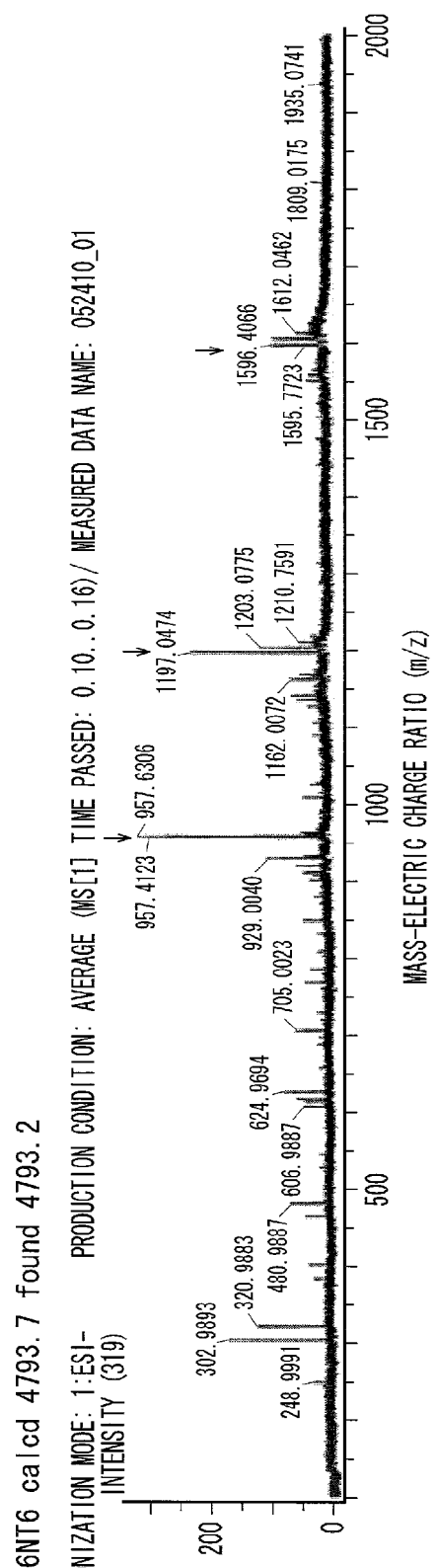
FIG. 1 is a view showing a mass spectrum of a DNA probe in accordance with an example of the present invention.

One embodiment of the present invention is described below in detail with reference to the attached drawings.

In this specification, the terms "phosphoramidite compound" and "compound" each includes a tautomer thereof, a stereoisomer thereof, a salt thereof, and the like.

[Compound]

A compound of the present invention will be described.

The compound of the present invention is a phosphoramidite compound (hereinafter, referred to also as "dye-containing phosphoramidite compound") which contains a dye (fluorescence dye) exhibiting an exciton effect, or a synthetic intermediate thereof. The compound of the present invention is represented by the following formula (1), (2), or (3).

[Chem. 9]

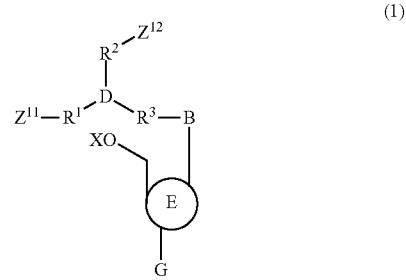

(1)

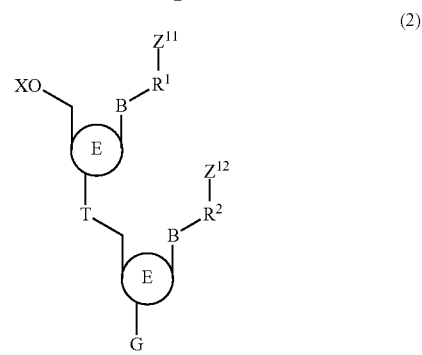

(2)

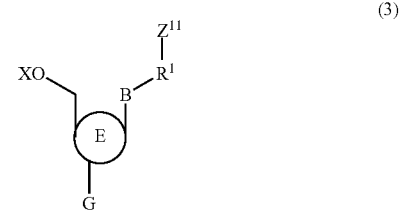

(3)

In the above formulae (1), (2), and (3), B is an atomic group having a basic skeleton. Examples of the atomic group having a basic skeleton encompass atomic groups having a natural nucleic acid basic (adenine, guanine, cytosine, thymine, or uracil) skeleton or an artificial nucleic acid basic skeleton.

B preferably is a pyrimidine base having a skeleton which is represented by the following formula (14), a purine base having a skeleton which is represented by the following formula (15), or derivatives thereof.

[Chem. 10]

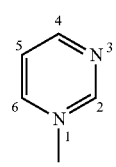

(14)

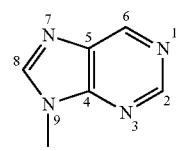

(15)

In the above formula (14), a first N-atom may have a covalent bond attaching to E in any one of the above formulae (1) to (3), and any one of atoms other than the first N-atom is optionally attached to (optionally forms a covalent bond with) a linker (i.e., $R^1$, $R^2$, $R^3$, or D) which links to a dye ($Z^{11}$ or $Z^{12}$). It is particularly preferable that a fifth atom is attached to the linker.

In the above formula (14), at least one carbon atom of atoms which constitute a six membered-ring may be substituted by an N, S, or O atom, and at least one nitrogen atom may be substituted by a C, S, or O atom. The N, C, S, or O atom may have an electric charge, a hydrogen atom, or a substituent.

In the above formula (15), a ninth N-atom have a covalent bond attaching to E in any one of the above formulae (1) to (3), and any one of atoms other than the ninth N-atom is optionally attached to (form a covalent bond with) a linker (i.e., $R^1$, $R^2$, $R^3$, or D) which links with a dye ($Z^{11}$ or $Z^{12}$). It is particularly preferable that an eighth atom is attached to the linker.

In the above formula (15), at least one carbon atom of atoms which form a five membered-ring and a six membered-ring, preferably form the five membered-ring, may be substituted by an N, S, or O atom, and at least one nitrogen atom may be substituted by a C, S, or O atom. The N, C, S, or O atom may have an electric charge, a hydrogen atom, or a substituent.

In the above formulae (1), (2), and (3), E is an atomic group having a deoxyribose skeleton or a ribose skeleton, or is a derivative thereof. It is preferable that E is an atomic group having a main chain structure of DNA, modified DNA, RNA, or modified RNA because synthesis can be easily carried out.

For example, in the above formulae (1) and (3), it is preferable that an atomic group represented by the following formula (1a) be an atomic group represented by the following formula (4) or (5).

[Chem. 11]

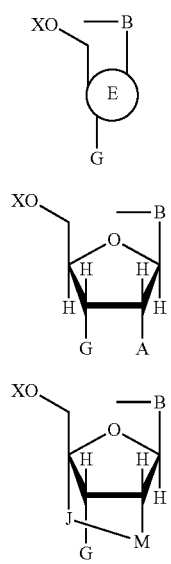

In the above formulae (4) and (5), A is a hydrogen atom, hydroxyl group, an alkyl group, an alkoxy group, or an electron attracting group. Examples of the alkyl group or the alkoxy group encompass a methoxy group. Examples of the electron attracting group encompass a halogen. M and J are independently $CH_2$, NH, O, or S.

For example, in the above formula (2), it is preferable that an atomic group represented by the following formula (2a) be an atomic group represented by the following formula (6) or (7).

[Chem. 12]

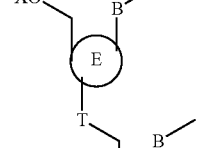

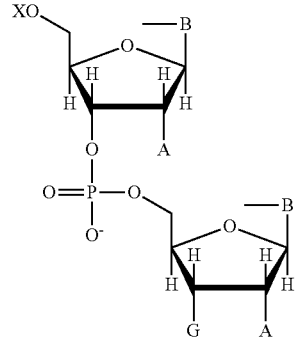

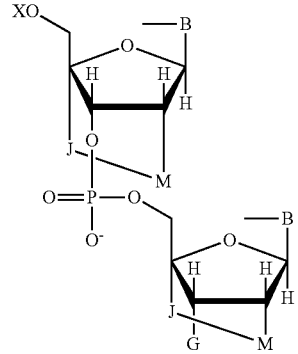

In the above formulae (6) and (7), A is a hydrogen atom, a hydroxyl group, an alkyl group, an alkoxy group, or an electron attracting group. Example of the alkyl group or the alkoxy group encompass a methoxy group. Example of the electron attracting group encompass halogens. M and J are independently $CH_2$, NH, O, or S.

In the above formulae (1), (2), and (3), $Z^{11}$ and $Z^{12}$ are independently atomic groups each having fluorescence (hereinafter, referred to also as "dye") and exhibiting an exciton effect. Further, $Z^{11}$ and $Z^{12}$ are each an uncharged atomic group. $Z^{11}$ and $Z^{12}$ may be identical to or different from each other.

The "exciton effect (exciton coupling)" (which is called also as "exciton coupling effect") is caused in such a way that $Z^{11}$ and $Z^{12}$ gather to be parallel with each other, or any one of $Z^{11}$ and $Z^{12}$ and another atomic group(s) gather to be parallel with one another, and form an H-aggregate. The wording "exhibiting an exciton effect" means that the atomic group emits fluorescence in a case where the exciton effect does not appear, whereas the atomic group quenches fluorescence in a case where the exciton effect appears. The exciton effect is considered to appear in such a way that (i) excited states of the atomic groups represented by $Z^{11}$ and $Z^{12}$ are split into two energy levels by Davydov splitting in a case where $Z^{11}$ and $Z^{12}$ form the H aggregate, (ii) the excited state becomes a higher energy level, (iii) the excited state is subjected to internal conversion to thereby become a lower energy level, and (iv) emission of light is thermally inhibited. Note, however, that the above description does not limit the present invention.

The wording "uncharged" means that the atomic group does not have an electric charge (positive charge or negative charge) in at least an aprotic solvent. To put it another way, the wording means that the atomic groups, which are represented by $Z^{11}$ and $Z^{12}$, have a small dipole moment. Note that the atomic groups, which are represented by $Z^{11}$ and $Z^{12}$, are not limited provided that the atomic groups have no electric charge in an aprotic solvent. The atomic group may be polarized to thereby have an electric charge in a protic solvent. The "aprotic solvent" indicates, for example, acetonitrile and N,N-dimethylformamide, and the "protic solvent" indicates, for example, water.

$Z^{11}$ and $Z^{12}$ may, for example, are independently atomic groups represented by the following formula (12).

[Chem. 13]

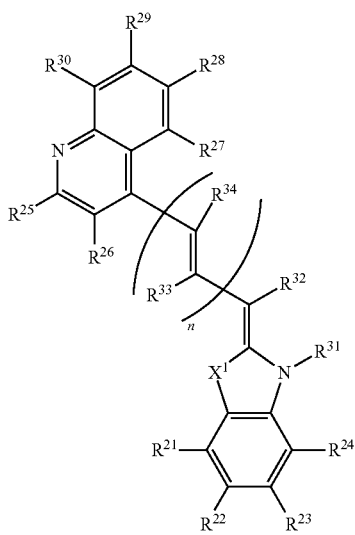

(12)

In the above formula (12), $X^1$ is O, S, Se, or Te, and preferably is O or S.

In the above formula (12), n is zero or a positive integer. This n is preferably 5 or less (for example, an integer of zero to 2, and more preferably zero or 1).

In the above formula (12), $R^{21}$ to $R^{30}$, $R^{32}$ to $R^{34}$ are independently hydrogen atoms, halogens, lower alkyl groups, lower alkoxy groups, nitro groups, or amino groups.

The lower alkyl group may be, for example, a C1 to C6 linear or branched alkyl group. The lower alkoxy group may be, for example, a C1 to C6 linear or branched alkoxy group.

$R^{28}$ and $R^{29}$ is optionally attached to each other. That is, $R^{28}$ and $R^{29}$ is optionally attached to each other, thereby forming a cyclic structure. The cyclic structure is, for example, an aryl group. Further, the cyclic structure or the aryl group optionally has a substituent.

In the above formula (12), $R^{31}$ is a linking group which is attached to $R^1$ or $R^2$ in the above formula (1), (2), or (3), or is a linking group which is attached to NH in the following formula (8), (9), (10), or (11). $R^{31}$ preferably has a main chain having a chain length of two or more atoms. Further, an upper limit of the chain length of the main chain is not particularly set, however, the upper limit of the chain length is preferably 100 or less atoms, more preferably 50 or less atoms, further more preferably 30 or less atoms, and particularly preferably 10 or less atoms.

It is preferable that $R^{31}$ be a C2 or more polymethylene carbonyl group and a carbonyl group moiety of $R^{31}$ are attached to $R^1$ or $R^2$ in the above formula (1), (2), or (3) or to NH in the following formula (8), (9), (10), or (11).

In the above formula (12), in a case where n is an integer of 2 or more, a plurality of $R^{33}$ may be identical to or different from each other, and a plurality of $R^{34}$ may be identical to or different from each other.

$Z^{11}$ and $Z^{12}$ are, for example, dyes represented by the following formulae (17) to (20).

[Chem. 14]

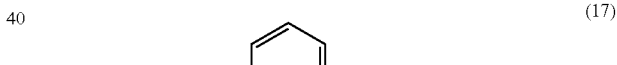

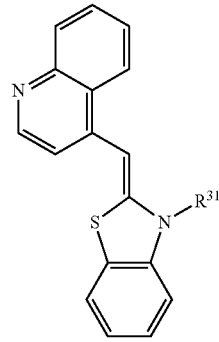

(17)

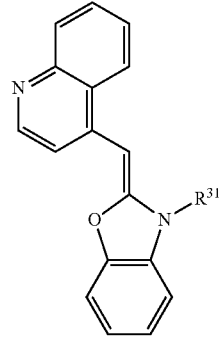

(18)

(19)

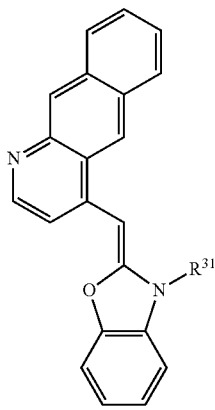

(20)

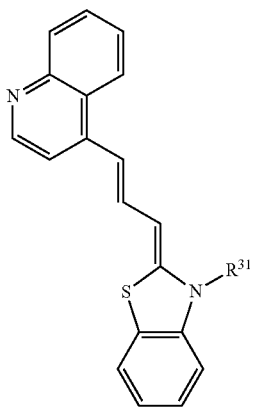

As $R^{31}$ in the above formulae (17) to (20), the examples of $R^{31}$ exemplified in the above formula (12) can be used.

$Z^{11}$ and $Z^{12}$ may are independently atomic groups represented by the following formula (28) or (29).

[Chem. 15]

(28)

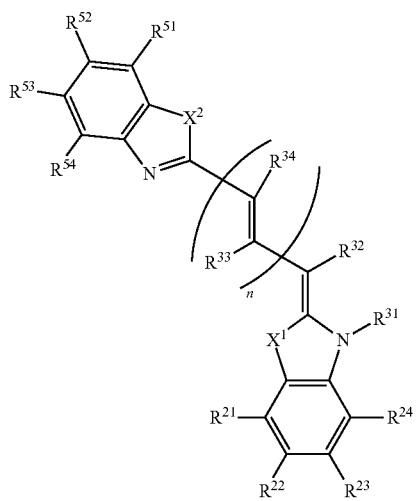

(29)

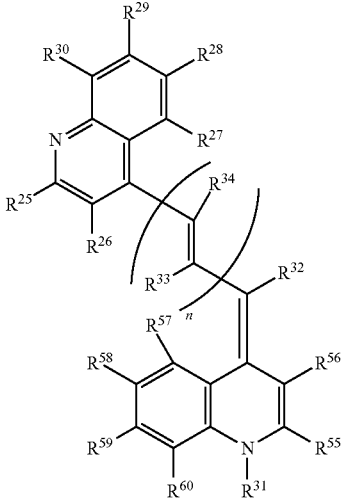

As $R^{21}$ to $R^{34}$, $X^1$, and n in the above formulae (28) and (29), the examples of $R^{21}$ to $R^{34}$, $X^1$, and n exemplified in the above formula (12) can be used.

In the above formula (28), $X^2$ is O, S, Se, or Te, and preferably O or S, Note that $X^1$ and $X^2$ may be identical to or different from each other.

In the above formulae (28) and (29), $R^{51}$ to $R^{60}$ identically are a hydrogen atom, a halogen, a lower alkyl group, a lower alkoxy group, a nitro group, or an amino group. The lower alkyl group may be, for example, a C1 to C6 linear or branched alkyl group. The lower alkoxy group may be, for example, a C1 to C6 linear or branched alkoxy group.

$R^{58}$ and $R^{59}$ is optionally attached to each other. That is, $R^{58}$ and $R^{59}$ is optionally attached to each other, thereby forming a cyclic structure. The cyclic structure is, for example, an aryl group. Further, the cyclic structure or the aryl group may optionally have a substituent.

$Z^{11}$ and $Z^{12}$ may are independently atomic groups represented by any one of the above formulae (12), (28), and (29).

In the above formulae (1), (2), and (3), examples of X encompass a hydrogen atom, a protecting group for protecting a hydroxyl group, the protecting group being deprotectable by an acid, a phosphate group, a diphosphate group, and a triphosphate group. The protecting group for protecting a hydroxyl group, which is deprotectable by an acid, is, for example, a dimethoxytrityl group (DMTr group).

In the above formulae (1), (2), and (3), G is a phosphoramidite group represented by the following formula (33) or a hydroxyl group.

[Chem. 16]

(33)

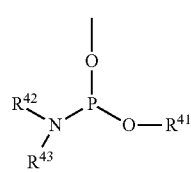

In the above formula (33), $R^{41}$ is a protecting group for protecting a phosphate group, and is, for example, a cyanoalkyl group. A cyanoethyl group is particularly preferable.

In the above formula (33), $R^{42}$ and $R^{43}$ are independently alkyl groups or aryl groups. The alkyl group is, for example, a C1 to C6 alkyl group, and an isopropyl group is particularly preferable. The aryl group is, for example, a C6 to C10 aryl group, and a phenyl group is particularly preferable.

In the above formulae (1), (2), and (3), $R^1$ and $R^2$ are independently linkers each having a main chain. An atom forming the main chain of $R^1$ or $R^2$ may optionally have a substituent. $R^3$ may be present as a linker having a main chain, and may be absent. In a case where $R^3$ has a main chain, an atom for forming the main chain may optionally has a substituent.

The numbers of atoms in chain lengths (the numbers of main chain atoms) forming the main chains of $R^1$ and $R^2$ and, if $R^3$ has a main chain, the number of atoms in chain length forming the main chain of $R^3$ are independently positive integers. It is preferable that the numbers of main chain atoms in chain lengths of $R^1$, $R^2$, and $R^3$ are independently integers of two or more. An upper limit of the number of main chain atoms in chain length is not particularly limited, however, is preferably 100 or less, more preferably 30 or less, further preferably 10 or less.

The main chains of $R^1$, $R^2$ and $R^3$ may contain at least one of C, N, O, S, P, and Si, and may have at least one of a single bond, a double bond, a triple bond, an amide bond, an ester bond, a disulfide bond, an imino group, an ether bond, a thioether bond, and a thioester bond. Further, $R^1$, $R^2$, and $R^3$ may be identical to or different from each other.

In the above formulae (1), (2), and (3), D may be $CR^{11}$, N, P, P=O, B (boron atom), or $SiR^{11}$, and $R^{11}$ may be a hydrogen atom, an alkyl group, or an arbitrary substituent. D may be absent.

In the above formulae (1), (2), and (3), in a case where $R^3$ does not exist and D exists, D may be directly attached to B. In a case where $R^3$ exists and D does not exist, $R^1$ and $R^2$ may be directly attached to $R^3$. In a case where both $R^3$ and D do not exist, $R^1$ and $R^2$ may be directly attached to B.

In the above formulae (1), (2), and (3), T is phosphate bridge. In this phosphate bridge, one or more oxygen atom(s) may be substituted by a sulfur atom(s).

It is preferable that the compound of the present invention be a compound represented by the following formula (8), (9), (10), or (11).

[Chem. 17]

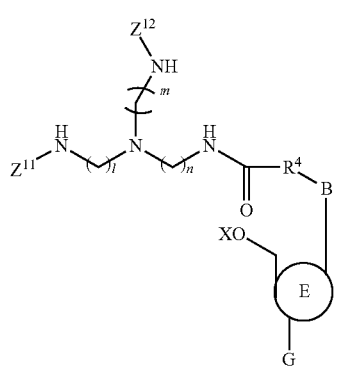

(8)

[Chem. 18]

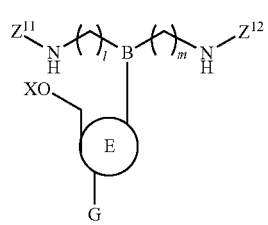

(9)

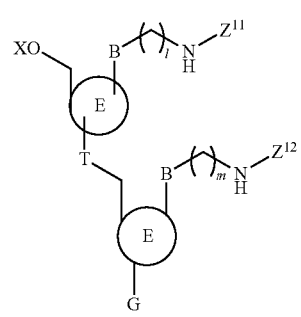

(10)

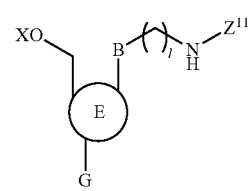

(11)

In the above formula (8), (9), (10), and (11), l, m, and n are independently positive integers. It is preferable that l, m, and n are independently integers of two or more. Upper limits of l, m, and n are not particularly limited, however, is preferably 100 or less, more preferably 30 or less, and further preferably 10 or less. Note that the upper limits of l, m, and n could be 5 or less, or 4 or less.

In the above formula (8), $R^4$ is a single bond, a double bond, or a triple bond, and may be absent. It is particularly preferable that $R^4$ is a double bond.

As B, E, $Zr^{11}$, $Z^{12}$, X, $R^{41}$, $R^{42}$, $R^{43}$, and T in the above formula (8), (9), (10), and (11), the examples of B, E, $Z^{11}$, $Z^{12}$, X, $R^{41}$, $R^{42}$, $R^{43}$, and T exemplified in the above formula (1) to (3) can be used.

The compound of the present invention is, for example, preferably a compound represented by the following formula (16).

[Chem. 19]

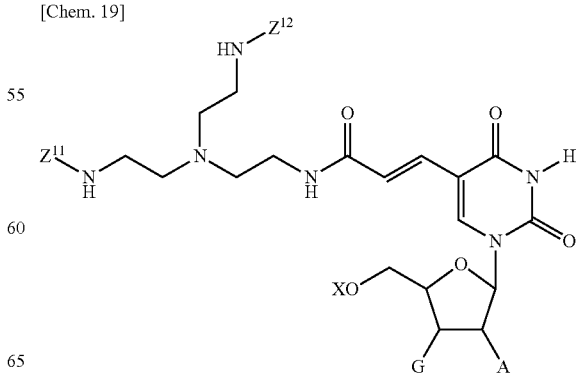

(16)

As X, G, $Z^{11}$, $Z^{12}$ in the above formula (16), the examples of X, G, $Z^{11}$, $Z^{12}$ exemplified in the above formulae (1) to (3) can be used. As A in the above formula (16), the examples of A exemplified in the above formulae (4) to (7) can be used.

The compound of the present invention whose G is a hydroxyl group can be used as a synthetic intermediate to synthesize a phosphoramidite form.

The compound of the present invention whose G is a phosphoramidite group represented by the above formula (33) (hereinafter, referred to also as "phosphoramidite compound of the present invention") can be used as a nucleoside substrate to be used for synthesizing a nucleic acid by a phosphoramidite method. A nucleic acid, which has been synthesized by using the phosphoramidite compound of the present invention, can be suitably used as, for example, a primer, a nucleic acid probe for detecting a nucleic acid, or a labeling substance. That is, the compound of the present invention can be used as a labeling reagent for a nucleic acid (nucleic acid labeling reagent).

[Method of Producing Phosphoramidite Compound]

The phosphoramidite compound of the present invention can be produced in various routes. The following description will discuss some examples of routes of producing a phosphoramidite compound of the present invention, however, the present invention is not particularly limited thereto.

For example, the phosphoramidite compound of the present invention may be produced by adding a linker constituted by $R^1$, $R^2$, D, $R^3$, etc. to a DMTr form of a nucleoside, adding $Z^{11}$ and $Z^{12}$ which are dyes, and then an amidate form is synthesized (see formulae (1) to (3)). Alternatively, the phosphoramidite compound of the present invention may be produced by adding, to a DMTr form of a nucleoside, $Z^{11}$ and $Z^{12}$ to which a linker constituted by $R^1$, $R^2$, D, $R^3$, etc. has been added in advance, and then an amidate form is synthesized (see formulae (1) to (3)).

For example, the phosphoramidite compound of the present invention can be produced by synthesizing a synthetic intermediate represented by the following formula (21), (22), or (23), and then an amidate form is synthesized.

[Chem. 20]

(21)

(22)

(23)

As B, E, $Z^{11}$, $Z^{12}$, X, $R^1$, $R^2$, $R^3$, D, and T in the above formula (21), (22), and (23), the examples of B, E, $Z^{11}$, $Z^{12}$, X, $R^1$, $R^2$, $R^3$, D, and T exemplified in the above formula (1) to (3) can be used.

In the present invention, because $Z^{11}$ and $Z^{12}$ are uncharged dyes in an aprotic solvent, $Z^{11}$ and $Z^{12}$ in the synthetic intermediates represented by the above formula (21), (22), or (23) have no electric charge in the aprotic solvent. It is therefore easy to synthesize an amidite form from those synthetic intermediates in the aprotic solvents. Thus the phosphoramidite compound of the present invention can be easily produced. Note that the kinds of aprotic solvents to be used as a solvent for synthesizing an amidite form are not particularly limited. Examples of the aprotic solvent encompass acetonitrile and N,N-dimethylformamide.

[Nucleic Acid]

The following description will discuss a nucleic acid of the present invention.

In this specification, the term "nucleic acid" means polynucleotide, and encompasses DNA, RNA, or the like. Examples of the nucleic acid also encompass an oligonucleic acid. The nucleic acid may be single-stranded or double-stranded. In this specification, the term "oligonucleic acid" means oligonucleotide, and is only required to be constituted by at least one nucleotide.

A length of the nucleic acid of the present invention is not particularly limited. For example, the length is preferably 10 bp or more but 10 kb or less, and more preferably 10 bp or more but 1 kb or less. The nucleic acid of the present invention may be an oligo-nucleic acid, and a length of the oligo-nucleic acid is not particularly limited. For example, the length of the oligo-nucleic acid is preferably 10 bp or more but 100 bp or less, and more preferably 10 bp or more but 50 bp or less, and further preferably 10 bp or more but 30 bp or less.

The nucleic acid of the present invention has an atomic group, represented by the following formula (25), (26), or (27), as a nucleotide moiety.

[Chem. 21]

(25)

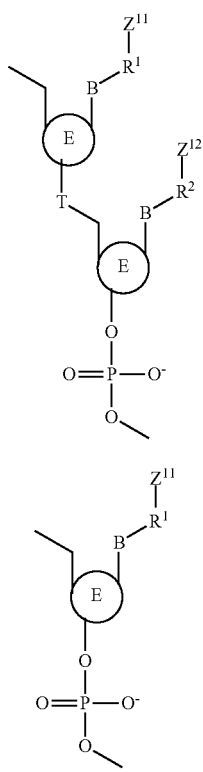

(26)

(27)

As B, E, $Z^{11}$, $Z^{12}$, $R^1$, $R^2$, $R^3$, D, and T in the above formula (25), (26), and (27), the examples of B, E, $Z^{11}$, $Z^{12}$, $R^1$, $R^2$, $R^3$, D, and T exemplified in the above formulae (1) to (3) can be used.

The nucleic acid of the present invention is required to have at least one atomic group, represented by the above formula (25) or (26), as a nucleotide moiety, but may have two or more atomic groups. Thus the nucleic acid of the present invention may have a single nucleotide moiety containing two dyes, or two nucleotide moieties which are consecutively aligned and each contain a single dye.

It is preferable that the nucleic acid of the present invention have both (A) an atomic group, represented by the above formula (27), as a nucleotide moiety and (B) another atomic group which has a structure exhibiting an exciton effect. The another atomic group may be, for example, an atomic group having any one of the examples cited as $Z^{11}$ and $Z^{12}$. It is preferable that the nucleic acid have at least two atomic groups, represented by the above formula (27), as a nucleotide moiety. Those two atomic groups may be consecutively aligned in the nucleic acid, or may be aligned so that other several nucleotides not containing a dye are sandwiched between the two atomic groups. It is preferable that the two atomic groups be aligned so that the dyes of the two atomic groups are gathered to exhibit the exciton effect.

It is preferable that the nucleic acid of the present invention be produced with use of the phosphoramidite compound of the present invention. The nucleic acid, which is produced with use of the phosphoramidite compound of the present invention, has, as a component, a moiety other than the phosphoramidite group in the phosphoramidite compound (which moiety is hereinafter referred to also as "dye-containing nucleoside").

That is, the nucleic acid of the present invention contains a dye exhibiting the exciton effect, and can be suitably used as a probe (nucleic acid probe) for detecting a nucleic acid, which is an object to be detected, by using the exciton effect. The nucleic acid of the present invention may constitute only a part of such a probe. By using such a nucleic acid probe, it is easily possible to detect a nucleic acid, which is an object to be detected, by observing (i) fluorescence emitted from the dye of the nucleic acid of the present invention and (ii) quenching caused by the exciton effect.

The nucleic acid of the present invention can be suitably used as a labeling substance in which the fluorescence emitted from the dye of the nucleic acid is used. For example, the labeling substance may be used for dying a tissue. The nucleic acid of the present invention can be further suitably used as a primer (e.g., a primer for PCR).

As described above, the nucleic acid of the present invention may be used as a primer, a probe, or a labeling substance for use in research, clinical activity, diagnosis, detection of genes in vitro, detection of genes in vivo, or the like.

In a case where the nucleic acid is synthesized with use of the phosphoramidite compound of the present invention, among the phosphoramidite compounds of the present invention, a phosphoramidite compound containing two dyes represented by the above formula (1) or (2) may be used in the amount of at least one molecule to synthesize the nucleic acid. Thus the nucleic acid has one molecule of nucleoside having two dyes, or two molecules of nucleosides which are consecutively aligned and each contain a single dye.

Among the phosphoramidite compounds of the present invention, a phosphoramidite compound containing a dye, which is represented by the above formula (3), is preferably used together with another compound which has an atomic group exhibiting the exciton effect in order to synthesize the nucleic acid. The another compound may be a compound having, for example, any one of the examples cited as $Z^{11}$ and $Z^{12}$. The nucleic acid may be synthesized by using at least two molecules of the above compound containing a dye.

In the following description, in a case where the nucleic acid of the present invention is a nucleic acid probe for detecting a nucleic acid (DNA, RNA, etc.) which is an object to be detected, a principle of detection of the nucleic acid which is an object to be detected will be described. As described above, the nucleic acid probe contains at least two dyes having the exciton effect. In a case where the nucleic acid probe is single-stranded, the dyes are associated with each other and therefore produce an exciton coupling effect. This results in quenching. Meanwhile, in a case where the nucleic acid probe is double-stranded, i.e., the nucleic acid probe is bound to a nucleic acid which is an object to be detected, the dyes intercalate into or form a groove binding with such a double stranded nucleic acid, and therefore an exciton coupling is canceled. This results in emission of fluorescence. By detecting the emission of the fluorescence, it is possible to detect a nucleic acid.

The nucleic acid of the present invention may contain at least two regions each containing nucleoside (dye-containing nucleoside) which is derived from the phosphoramidite compound of the present invention. The regions of the nucleic acid are preferably formed so that a dye of a dye-containing nucleoside which is contained in a certain region and another dye of a dye-containing nucleoside which is contained in another region do not exhibit the exciton effect. It is also preferable that the dyes of the dye-containing nucleosides in those regions emit different wavelengths of fluorescence.

As described above, the nucleic acid of the present invention contains different dyes. Therefore, in a case where the nucleic acid is used as a nucleic acid probe, it is possible to detect which region of the nucleic acid probe is attached to the nucleic acid which is an object to be detected by simultaneously observing emission and quenching of the dyes. That is, in a case where only a part of the nucleic acid probe forms, for example, a double strand with the nucleic acid which is the object to be detected, it is possible to detect, for example, which sequence of the nucleic acid probe forms the double strand.

For example, dye-containing nucleoside which contains a red dye and dye-containing nucleoside which contains a blue dye may be introduced into different regions, apart from each other, of a nucleic acid probe. In a case where the nucleic acid probe is used to detect a nucleic acid and only blue color is emitted, it is found that a region which has introduced the dye-containing nucleoside containing the blue dye hybridizes the nucleic acid which is an object to be detected, however, a region which has introduced the dye-containing nucleoside containing the red dye does not hybridize the nucleic acid which is the object to be detected.

In the present invention as described above, it is possible to introduce different dyes into a single nucleic acid by the above method. Therefore, by using the present invention, it is possible to produce a nucleic acid probe for detecting various nucleic acid structures. For example, the nucleic acid probe can be used to investigate gene translocation related to cancer, a splicing site of an RNA, etc., and can be preferably used to diagnose various diseases, solve causes of diseases, etc.

In a case where the nucleic acid of the present invention is used as a probe for detecting hybridization with a complementary strand, the nucleic acid is used under an environment of preferably pH of 10.5 or less, more preferably pH of 9 or less, and further preferably pH of 8 or less in order to obtain a stronger fluorescence intensity. Note that, in each case, background noise from a non-hybridized probe is sufficiently suppressed.

[Method of Producing Nucleic Acid]

The following description will discuss a method of the present invention of producing a nucleic acid.

The method of the present invention of producing a nucleic acid includes a step (adding step) of adding a dye-containing nucleoside, the step carrying out a condensation reaction of the above-described phosphoramidite compound of the present invention and oligo-nucleic acid. Performing this dye-containing nucleoside adding step can add, to an oligo-nucleic acid, a nucleoside (dye-containing nucleoside) which has an atomic group having fluorescence and exhibiting an exciton effect.

The dye-containing nucleoside adding step is a step of causing the phosphoramidite compound of the present invention (that is, a dye-containing phosphoramidite compound) to undergo a condensation reaction with a 5'-hydroxyl group of a nucleotide in an oligo-nucleic acid by a phosphoramidite method. Performing this step adds a dye-containing nucleoside to an oligo-nucleic acid to synthesize an oligo-nucleic acid that contains a dye-containing nucleoside.

The dye-containing nucleoside adding step preferably causes the dye-containing phosphoramidite compound and the oligo-nucleic acid to react with each other at room temperature for 2 minutes to 20 minutes. This step can suitably use, for other reaction conditions, conditions normally used in a phosphoramidite method.

The method of the present invention of producing a nucleic acid may further include, before the dye-containing nucleoside adding step, a step of obtaining a phosphoramidite compound by synthesizing an amidite form from the compound of the present invention in which G is a hydroxyl group.

The present invention may be implemented by incorporating, into a publicly known method of producing a nucleic acid, the above dye-containing nucleoside adding step. The publicly known method of producing a nucleic acid is, for example, a method of repeating, predetermined times, a set including (i) a nucleoside adding step of adding a normal nucleoside substrate to an oligo-nucleic acid by a phosphoramidite method, (ii) a deprotecting step of deprotecting the oligo-nucleic acid synthesized during the nucleoside adding step, and (iii) a purifying step of purifying the oligo-nucleic acid deprotected during the deprotecting step. The method of the present invention of producing a nucleic acid may be a method in which the nucleoside adding step of at least one set in the publicly known method of producing a nucleic acid is replaced with the above dye-containing nucleoside adding step.

The present invention may be a method in which the nucleoside adding step of each of a plurality of sets in the publicly known method of producing a nucleic acid is replaced with the above dye-containing nucleoside adding step. This arrangement makes it possible to produce a nucleic acid including a plurality of dye-containing nucleosides derived from the compound of the present invention. The plurality of sets may be (i) sets that are performed continuously or (ii) sets that are performed with one or more other sets performed in-between. This arrangement makes it possible to produce a nucleic acid having at least two regions in each of which the nucleic acid contains a dye-containing nucleoside derived from the compound of the present invention.

In the case where the production method of the present invention includes a plurality of steps of adding a dye-containing nucleoside, such a plurality of steps of adding a dye-containing nucleoside may involve phosphoramidite compounds containing respective dyes different from each other. This arrangement makes it possible to introduce, into a single nucleic acid, a plurality of dyes different from each other, thus making it possible to produce a nucleic acid containing a plurality of dyes different from each other.

The above dye-containing nucleoside adding step, nucleoside adding step, deprotecting step, and purifying step may, for example, each be performed by a publicly known method under publicly known conditions with use of a publicly known device. The above steps may, for example, be performed with use of a publicly known automatic nucleic acid synthesizing device. The method of the present invention of producing a nucleic acid can thus use a publicly known nucleic acid synthesizing device or the like.

As described above, the production method of the present invention can be used to produce a nucleic acid including a dye-containing nucleoside, that is, a nucleic acid of the present invention.

The present invention does not require the two synthesizing steps, i.e., the synthesizing step of synthesizing a DNA oligomer and a synthesizing step of synthesizing the DNA oligomer with fluorescent molecules to introduce the fluorescent molecules. The present invention thus facilitates producing a nucleic acid which contains a dye exhibiting the exciton effect. Further, the present invention uses, for DNA synthesis, a nucleoside containing a dye introduced therein in advance. The present invention can thus avoid the risk of synthesis of an imperfect nucleic acid not containing a desired number of dyes introduced therein.

[Kit for Producing Nucleic Acid]

The present invention provides a kit for producing the nucleic acid of the present invention, the kit including the above compound of the present invention. The use of this kit allows the above method of producing a nucleic acid to be performed with use of the phosphoramidite compound of the present invention (that is, a dye-containing phosphoramidite compound), thereby facilitating the production of a nucleic acid.

The kit of the present invention may include a plurality of kinds of dye-containing phosphoramidite compounds containing respective dyes different in kind from each other. The kit of the present invention may further include any nucleoside containing no dye. Such a nucleoside is preferably included in such a form as to be suitably used for synthesis of a nucleic acid (for example, as a phosphoramidite form). The kit of the present invention may further include, for example, (i) a device for synthesizing a nucleic acid, (ii) a reagent for use in the synthesis of a nucleic acid, (iii) a detection reagent for detecting a nucleic acid with use of a produced nucleic acid, and (iv) an instruction manual for the kit (the instruction manual describing a specific technique for producing a nucleic acid with use of the kit).

The present invention is not limited to the embodiments described above, and may be modified within the scope of claims. The technical scope of the present invention also includes any embodiment obtained by appropriately combining the technical means disclosed in different embodiments.

EXAMPLES

The Examples below used reagents, solvents and the like that were commercially available, and measured $^1$H and $^{13}$C NMR spectra with use of JNM-α400 (product name) available from JEOL Ltd. Coupling constants (J values) are expressed in hertz (Hz). Chemical shifts are expressed in ppm. As internal standards, (i) dimethyl sulfoxide (δ=2.48 in $^1$H NMR, δ=39.5 in $^{13}$C NMR) and (ii) methanol (δ=3.30 in $^1$H NMR, δ=49.0 in $^{13}$C NMR) were used. The Examples below measured an ESI mass spectrum with use of Bruker Daltonics APEC-II (product name) available from Bruker Daltonics.

Example 1

Synthesis of Fluorescence Dye

This Example synthesized, by the following reaction formulae (A) to (D), an NHS activator for a fluorescence dye (that is, an atomic group having fluorescence) represented by the following formula (24). The description below deals with a specific method used.

[Chem. 22]

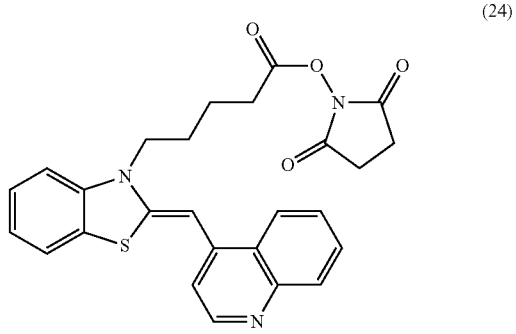

(24)

1-1: Synthesis of 1-(2-Carboxyethyl)quinolinium Bromide

[Chem. 23]

Reaction Formula (A)

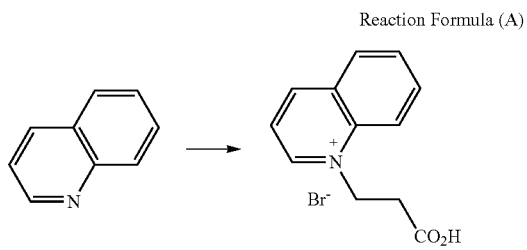

A mixture of quinoline (11.8 mL, 100 mmol) and 3-bromopropionic acid (15.3 g, 100 mmol) was heated and stirred at 150° C. for 10 minutes. Then, 500 mL of dichloromethane was added to this. The resulting solid was crushed into powder, which was stirred for 1 hour. Next, a white precipitate was filtered, washed with dichloromethane, and dried under reduced pressure. This produced the target compound as in the form of white powder of 20.7 g (73.7 mmol, 74%). The following shows measurement data for that target compound.

$^1$H NMR (DMSO-d$_6$): 12.69 (br, 1H), 9.62 (dd, J=5.9, 1.5 Hz, 1H), 9.33 (d, J=8.3 Hz, 1H), 8.63 (d, J=8.8 Hz, 1H), 8.50 (dd, J=8.3, 1.5 Hz, 1H), 8.28-8.24 (m, 1H), 8.20 (dd, J=8.3, 5.9 Hz, 1H), 8.06-8.02 (m, 1H), 5.27 (t, J=7.0 Hz, 2H), 3.09 (t, J=7.0 Hz, 2H);

$^{13}$C NMR (DMSO-d$_6$): 171.4, 150.7, 147.7, 137.3, 135.7, 130.8, 129.8, 129.6, 121.9, 118.9, 53.2, 33.3

1-2: Synthesis of 4-{[3-(4-Carboxybutyl) Benzothiazol-2-ylidene]methyl}-1-(2-Carboxyethyl)quinolinium Bromide

[Chem. 24]

Reaction Formula (B)

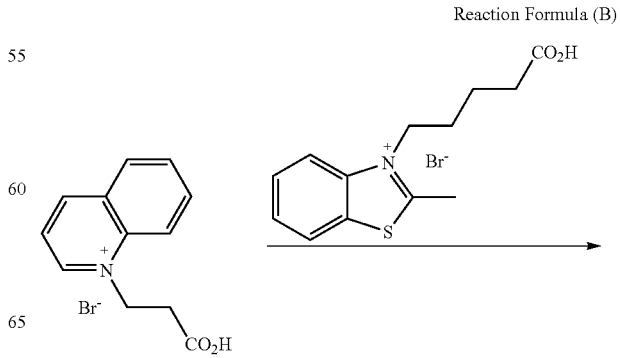

-continued

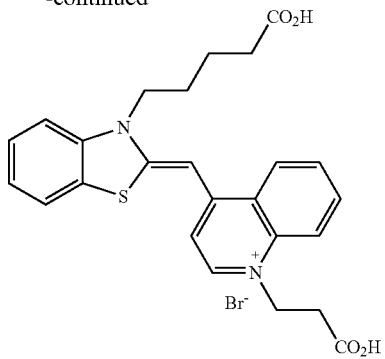

First, 3-(4-carboxybutyl)-2-methylbenzothiazolium bromide (17.0 g, 51.5 mmol) and 1-(2-carboxyethyl)quinolinium bromide (14.5 g, 51.5 mmol) were suspended in 300 mL of dichloromethane. Then, triethyl amine (72 mL, 515 mmol) was added to the suspension, and the resulting mixture was stirred at 25° C. for 16 hours. Next, the solvent was evaporated under reduced pressure, and 500 mL of acetone was added. A precipitate produced thereby was filtered, washed with acetone, and dried under reduced pressure.

Resulting powder was washed with 500 mM of distilled water. A precipitate was filtered, washed further with distilled water, and then dried under reduced pressure. This powder was washed with 500 mL of acetonitrile in a similar manner and dried under reduced pressure. This produced 8.31 g (15.7 mmol, 30%) of red powder as a target compound. The following shows measurement data for that target compound.

$^1$H NMR (CD$_3$OD): 8.53 (d, J=7.8 Hz, 1H), 8.42 (d, J=7.3 Hz, 1H), 8.01 (d, J=8.6 Hz, 1H), 7.91-7.88 (m, 1H), 7.79 (d, J=7.6 Hz, 1H), 7.71 (t, J=7.7 Hz, 1H), 7.59 (d, J=8.1 Hz, 1H), 7.55-7.52 (m, 1H), 7.34-7.30 (m, 2H), 6.80 (s, 1H), 4.75 (t, J=6.6 Hz, 2H), 4.48 (t, J=7.7 Hz, 2H), 2.81 (t, J=6.6 Hz, 2H), 2.41 (t, J=7.0 Hz, 2H), 1.97-1.91 (m, 2H), 1.87-1.81 (m, 2H);

$^{13}$C NMR (CD$_3$OD): 178.0, 176.4, 161.1, 150.7, 145.6, 141.2, 138.5, 134.4, 129.4, 128.2, 126.6, 126.0, 125.8, 125.7, 123.7, 118.7, 113.7, 109.5, 88.8, 53.2, 47.3, 37.2, 35.1, 27.7, 23.5

1-3: Synthesis of 4-{[3-(4-Carboxybutyl)Benzothiaazol-2-ylidene]methyl}quinoline

[Chem. 25]

Reaction Formula (C)

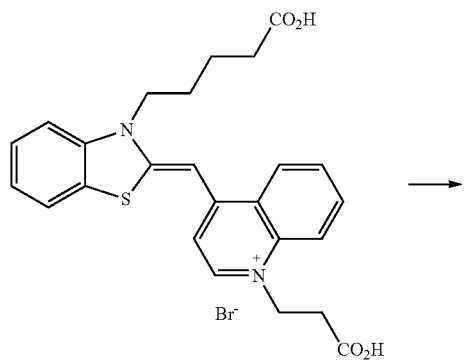

-continued

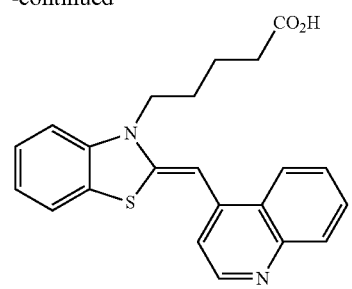

First, 4-{[3-(4-Carboxybutyl)benzothiazol-2-ylidene]methyl}-1-(2-carboxyethyl)quinolinium bromide (6.15 g, 11.6 mmol) and O-(benzotriazol-1-yl)-N,N,N',N'-tetramethyluronium hexafluorophosphate (13.2 g, 34.8 mmol) were suspended in 60 mL of DMF. Then, triethyl amine (9.7 mL, 69.7 mmol) was added to the suspension and stirred at 25° C. for 16 hours. Next, 10 mL of distilled water was added to the reaction solution, and stirred further for 30 minutes. After that, 500 mL of distilled water and 15 mL of an acetic acid were added to the reaction solution. A precipitate produced thereby was filtered, washed with distilled water, and dried under reduced pressure.

Then, 300 mL of methanol was added to red powder produced and mixed well. A precipitate was filtered and dried under reduced pressure. Next, 300 mL of dichloromethane was added to the resulting red powder and mixed well. A supernatant fluid was then disposed of by decantation. After that, 300 mL of acetone was added to the product. A precipitate produced thereby was filtered and dried under reduced pressure. This produced 2.24 g (5.95 mmol, 51%) of red powder as a target compound. The following shows measurement data for that target compound.

$^1$H NMR (DMSO-d$_6$): 12.18 (br, 1H), 8.65 (d, J=5.9 Hz, 1H), 8.51 (d, J=8.3 Hz, 1H), 7.89 (dd, J=8.3, 1.0 Hz, 1H), 7.83-7.79 (m, 2H), 7.66-7.62 (m, 1H), 7.51-7.41 (m, 3H), 7.23-7.20 (m, 1H), 6.68 (s, 1H), 4.41 (t, J=7.3 Hz, 2H), 2.32 (t, J=7.2 Hz, 2H), 1.83-1.77 (m, 2H), 1.73-1.81 (m, 2H);

$^{13}$C NMR (DMSO-d$_6$): 174.2, 153.5, 145.8, 144.9, 142.6, 140.5, 130.8, 127.4, 126.1, 124.7, 124.24, 124.19, 123.0, 122.8, 122.2, 111.0, 110.6, 85.8, 44.6, 33.2, 25.8, 21.7

1-4: Synthesis of 4-{[3-(4-Succinimidoxycarbonyl-butyl)-2(3H)-Benzothiazolylidene]methyl}quinoline

[Chem. 26]

Reaction Formula (D)

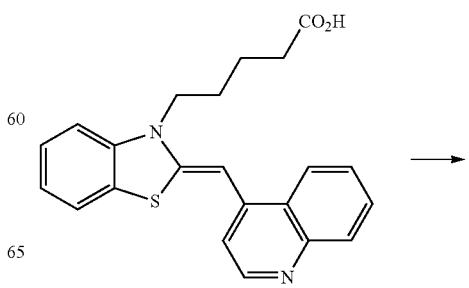

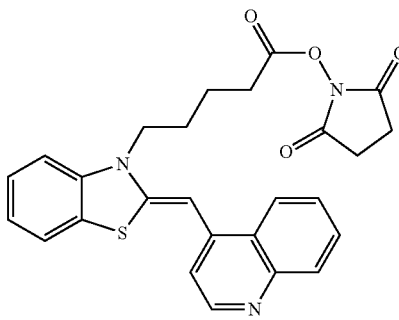

DMF (12 ml) was added to (i) 4-{[3-(4-carboxybutyl)-2 (3H)-benzothiazolylidene]methyl}quinoline (755 mg, FW 376.47), (ii) N-hydroxy succinimide (462 mg, FW 115.09), and (iii) N,N-diisopropyl carbodiimide (506 mg, FW 126.20). The mixture was stirred at 25° C. overnight. Then, 50 ml of each of methylene chloride and water was added to this, which was then subjected to liquid separation. An organic phase was washed with a saturated NaCl aqueous solution, dried with magnesium sulfate, and then filtered. A filtrate was concentrated by evaporation, to which diethyl ether was then added. A precipitate was filtered, washed with diethyl ether, and dried. Next, the dried precipitate was washed with chloroform and dried. This produced 227 mg (FW 473.54, yield: 24%) of red powder as a target compound. The following shows measurement data for that target compound.

$^1$H-NMR (DMSO-$d_6$): 8.68 (d, J=8.3 Hz, 1H), 8.60 (d, J=6.6 Hz, 1H), 8.02 (d, J=7.3 Hz, 1H), 7.91 (m, 2H), 7.74 (m, 2H), 7.60 (t, J=7.8 Hz, 1H), 7.45 (d, J=6.6 Hz, 1H), 7.39 (t, J=7.5 Hz, 1H), 6.89 (s, 1H), 4.63 (m, 2H), 2.83 (t, J=6.6 Hz, 2H), 2.77 (s, 4H), 1.89 (m, 4H);

$^{13}$C-NMR (DMSO-$d_6$): 170.2, 169.0, 158.3, 149.0, 140.8, 140.0, 137.8, 132.7, 128.1, 126.9, 125.0, 124.2, 123.6, 123.3, 122.8, 120.6, 112.7, 108.4, 87.2, 45.0, 29.8, 25.8, 25.4, 21.5;

HRMS (ESI) calcd for $C_{26}H_{24}N_3O_4S([M+H]^+)$ 474.15; found, 474, 12.

Example 2

Synthesis of Phosphoramidite Form

This Example synthesized, by the following reaction formulae (E) to (G), a phosphoramidite form (dye-containing phosphoramidite compound) of a nucleoside containing a fluorescence dye. The description below deals with a specific method used.

2-1: Synthesis of 5'O-DMTr-5-(2-[2-{N,N-bis(2-aminoethyl)}aminoethyl]carbamoyl-(E)-vinyl)-2'-deoxyuridine This Example first deprotected an amino group in a DMTr form of a nucleoside by the following reaction formula (E):

[Chem. 27]

Reaction Formula (E)

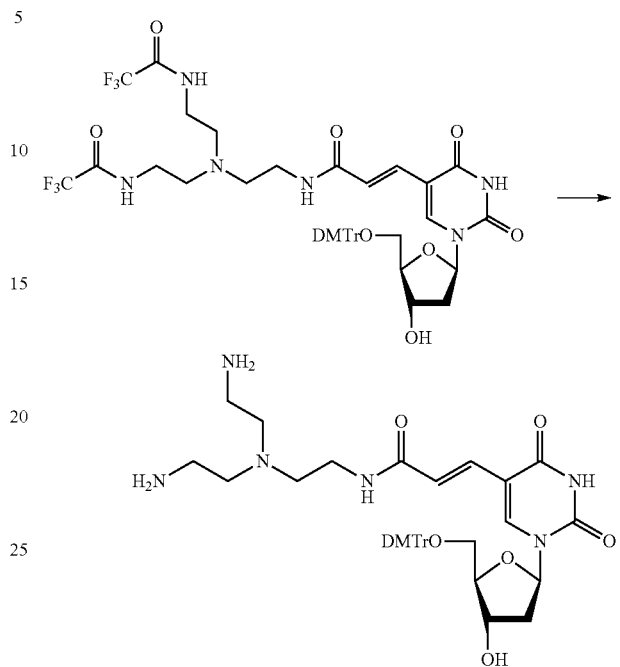

First, 5'-O-DMTr-5-(2-[2-{N,N-bis(2-trifluoroacetamido-ethyl)}aminoethyl]carbamoyl-(E)-vinyl)-2'-deoxyuridine (500 mg, FW 920.85) was added to a mixed solution of 10 ml of ammonia water (28%) and 10 ml of methanol, and the resulting mixture was stirred at 25° C. overnight. This reaction liquid was concentrated by evaporation and dissolved in a small amount of acetone, to which diethyl ether was then added. A precipitate produced thereby was filtered to be separated, washed with diethyl ether, and then dried. This produced 273 mg (FW 728.83, yield: 69%) of white powder as a target compound. The following shows measurement data for that target compound.

$^1$H-NMR (CD$_3$OD): 7.97 (s, 1H), 7.43 (m, 2H), 7.33-7.27 (m, 6H), 7.20 (t, J=7.2 Hz, 1H), 7.02 (d, J=3.7 Hz, 2H), 6.86 (td, J=2.2, 6.9 Hz, 4H), 6.20 (t, J=6.5 Hz, 1H), 4.40 (q, J=3.2 Hz, 1H), 4.08 (dd, J=3.5, 7.2 Hz, 1H), 3.76 (s, 6H), 3.39-3.27 (m, 4H), 3.03 (t, J=6.1 Hz, 4H), 2.81 (t, J=6.1 Hz, 4H), 2.65 (t, J=6.6 Hz, 2H), 2.47-2.33 (m, 2H);

$^{13}$C-NMR (CD$_3$OD): 169.3, 163.7, 160.2, 151.0, 146.1, 143.4, 137.1, 137.0, 134.6, 131.3, 131.2, 129.3, 128.9, 128.0, 122.4, 114.3, 110.8, 88.2, 88.0, 72.7, 65.0, 55.8, 54.5, 52.8, 41.8, 38.5, 38.4;

HRMS (ESI) calcd for $C_{39}H_{49}N_6O_8$ ([M+H]$^+$), 729.36; found, 729.3114.

2-2: Synthesis of Double Dye-Labeled Nucleoside

Next, this Example synthesized, by the following reaction formula (F), a DMTr form of a nucleoside containing a fluorescence dye.

[Chem. 28]
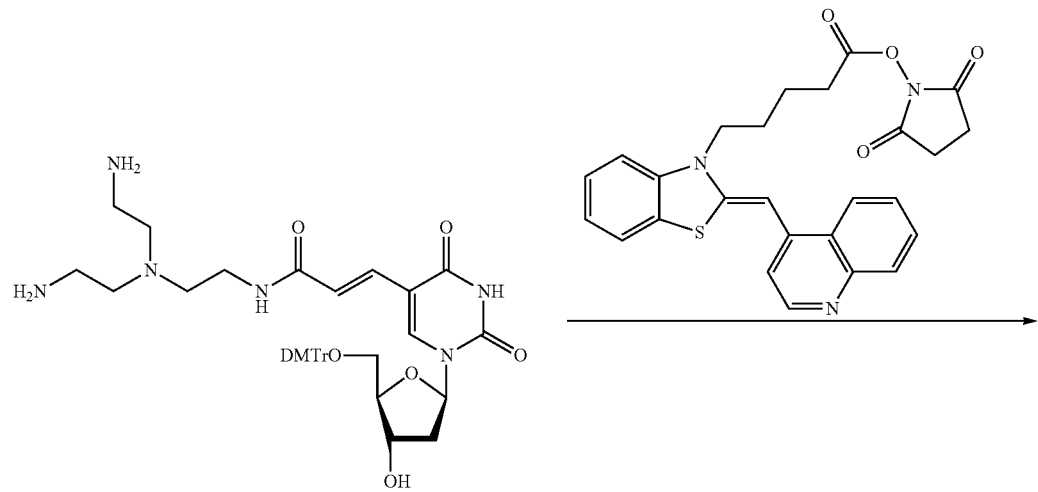
Reaction Formula (F)
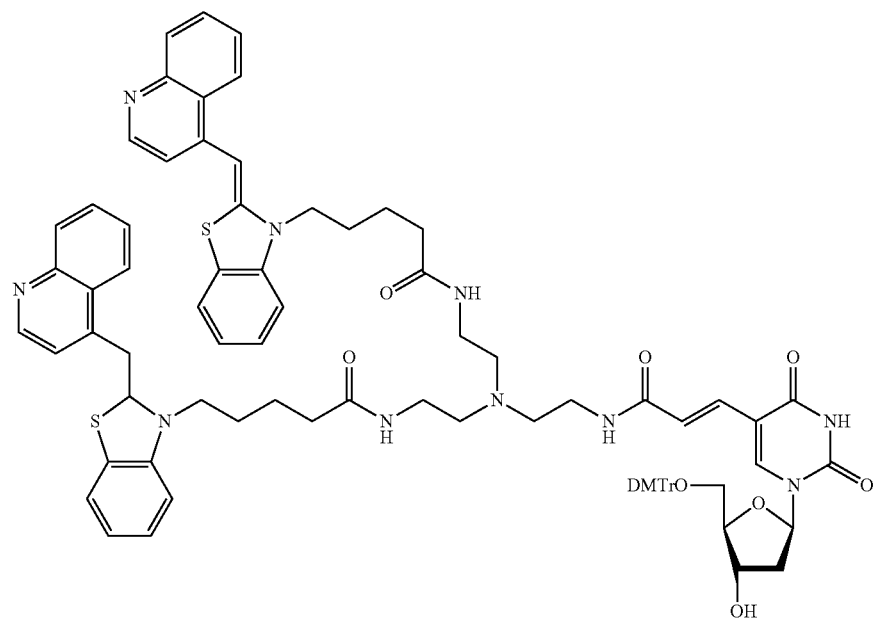

First, 13 ml of pyridine was added to (i) 5-O-DMTr-5-(2-[2-{N,N-bis(2-aminoethyl)}aminoethyl]carbamoyl-(E)-vinyl)-2'-deoxyuridine (232 mg, FW 728.83) and (ii) 4-{[3-(4-succinimidoxycarbonylbutyl)-2(3H)-benzothiazolylidene]methyl}quinoline (that is, an NHS activator for a dye) (331 mg, FW 473.54), and the resulting mixture was stirred at 25° C. overnight. The solvent was evaporated off, and the remaining was purified with use of a silica gel column (5% MeOH, 1% $Et_3N/CH_2Cl_2$). The solvent was evaporated off, and the remaining was dissolved in a small amount of acetone, to which diethyl ether was then added. Orange-colored powder produced thereby was filtered, washed with ether, and then dried. Thus 83 mg (FW 1445.75, yield: 18%) of a target compound was obtained. The following shows measurement data for that target compound.

HRMS (ESI) calcd for $C_{83}H_{85}N_{10}O_{10}S_2$ ([M+H]$^+$) 1445.59; found, 1445.49.

2-3: Synthesis of Amidite

Next, this Example synthesized, by the following reaction formula (G), a dye-containing phosphoramidite compound by synthesizing an amidite form from the DMTr form synthesized in 2-2 above in an aprotic solvent.

[Chem. 29]

Reaction Formula (G)

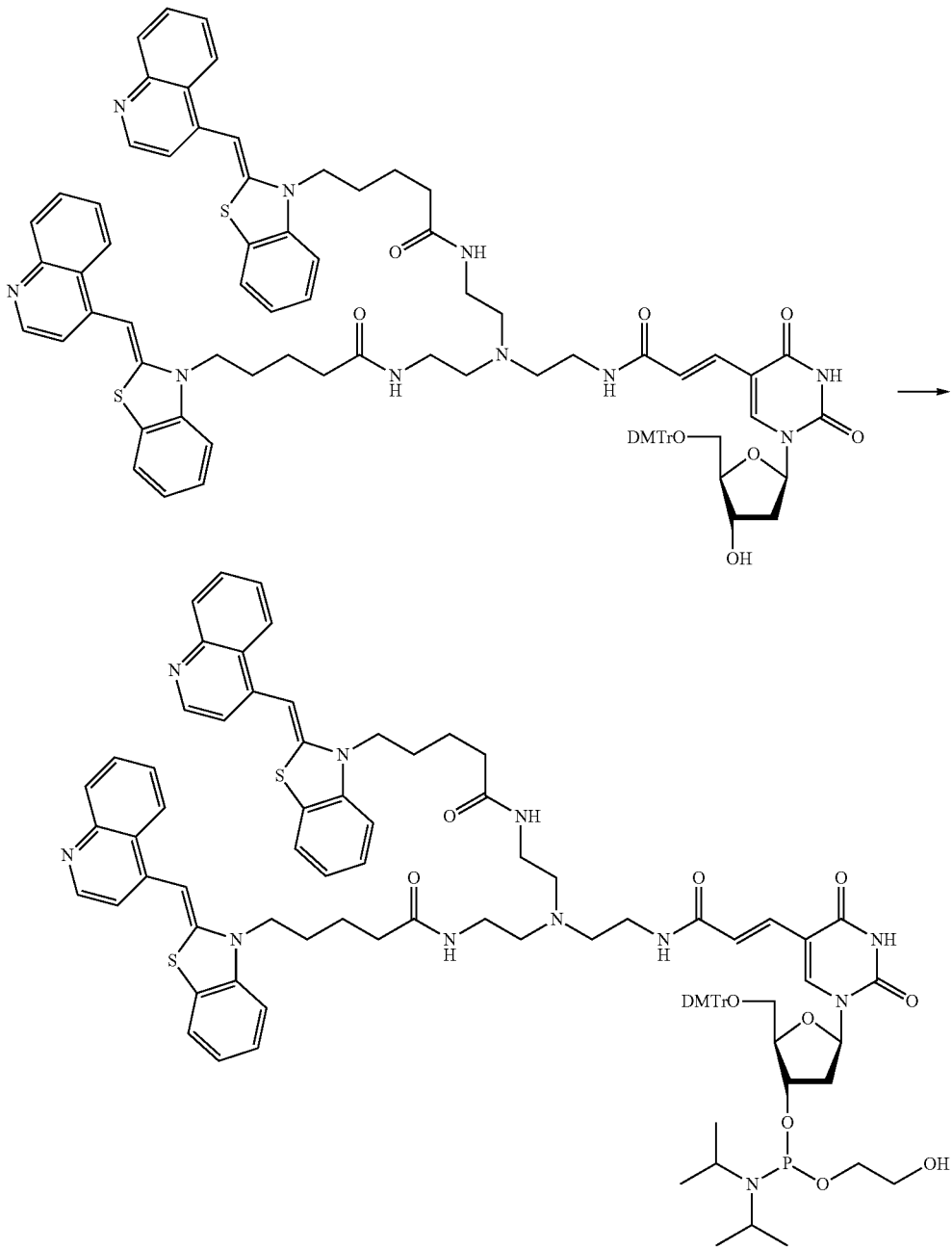

First, (i) 212 mg of a DMTr form (that is, the compound on the left side of the reaction formula (G) above) (FW 1445.75, 0.147 mmol), (ii) 21 mg of 1H-tetrazole (FW 70.05, 0.30 mmol), (iii) 4 mL of acetonitrile, and (iv) 2 mL of N,N-dimethylformamide (DMF) were mixed with one another. Then, 240 µL of an amidite agent (FW 301.41, d=0.949, 0.75 mmol) was added to the mixture. Thirty minutes later, a mixed solution of sodium bicarbonate water and ethyl acetate was added to the mixture, which was then subjected to liquid separation. Next, an organic phase was washed with a sodium chloride aqueous solution, dried with magnesium sulfate, and filtered. After that, a solvent was evaporated.

A phosphoramidite form produced thereby was dissolved in a solvent of DMF:acetonitrile=1:1 to provide a 0.1M solution, which was filtered and then used for a DNA synthesis in Example 3.

Example 3

DNA Probe

This Example synthesized, with use of the dye-containing phosphoramidite compound synthesized in Example 2, a DNA probe (nucleic acid) including a nucleoside containing a fluorescence dye. The description below deals with a specific method used.

3-1. DNA Synthesis

With use of a DNA synthesizer (392 DNA/RNA synthesizer (product name) available from Applied Biosystems), DNA probe 5'-d(TTTTTTNTTTTTT)-3' (SEQ ID NO:1) (where N is a nucleoside containing a fluorescence dye) was synthesized by solid phase synthesis. A nucleoside (N) containing a fluorescence dye was introduced over a reaction time of 15 minutes, whereas a nucleoside (T) containing no fluorescence dye was introduced over a reaction time of 2 minutes. The other conditions were conditions used in a normal phosphoramidite method. The DNA probe was cut out from a solid-phase carrier by a normally used method (that is, a method that uses 28% ammonia water). Further, deprotecting was performed at 25° C. overnight (for 16 hours).

3-2. Purifying of DNA Probe

Next, the synthesized DNA probe was purified with use of a reversed-phase HPLC (using Gilson Chromatograph, Model 305 (product name): an apparatus available from Gilson, Inc.). In the reversed-phase HPLC, the column used therein was CHEMCOBON D 5-ODS-Hcolumn (product name, 10×150 mm) and the solvent used therein was 100 mM TEAA buffer (pH7.0)/5-55% $CH_3CN$. The reversed-phase HPLC was performed with a gradient of 40 minutes and a flow rate of 3 mL/minute. UV absorption for 260 nm was monitored with use of UV detector Model 118 (product name) to detect the DNA probe.

The purified DNA probe was identified by a mass spectrum measurement involving an ESI method. FIG. 1 is a diagram illustrating a mass spectrum of a DNA probe in accordance with an example of the present invention. The DNA probe 5'-d(TTTTTTNTTTTTT)-3' (SEQ ID NO:1) (molecular formula $C_{182}H_{222}N_{34}O_{92}S_2P_{12}$) of this Example had a molecular weight of a calculated value of 4793.7 and a measured value of 4793.2.

As described above, the use of a phosphoramidite form of a nucleoside containing a fluorescence dye successfully facilitated synthesizing a DNA probe containing a fluorescence dye. Specifically, the results above show that while synthesizing a DNA probe involves repeating a set of a nucleoside adding step, a deprotecting step, and a purifying step to introduce a nucleoside, the use of the compound of the present invention in one set of the sets thus repeated facilitates producing a DNA probe containing a fluorescence dye.

The compound of the present invention, as described above, contains a fluorescence dye in advance. This eliminates the need to separately introduce a fluorescence dye after DNA synthesis. The results above therefore show that the present invention makes it possible to produce a DNA probe easily and with less work.

Example 4

UV Absorption Spectrum Measurement and Fluorescence Spectrum Measurement with Use of DNA Probe With use of the DNA probe synthesized in Example 3, a UV absorption spectrum measurement and a fluorescence spectrum measurement were performed. The UV absorption spectrum measurement was performed with use of Shimadzu UV-2550 (product name) spectro photometer available from Shimadzu Corporation, whereas the fluorescence spectrum measurement was performed with use of RF-5300 PC (product name) fluorescence spectro photometer.

First, a UV absorption measurement was performed for DNA probe 5'-d(TTTTTTNTTTTTT)-3' (SEQ ID NO:1) to determine its concentration (molar absorptivity $\epsilon$=105, 900 for 260 nm, and approximated to N=T).

The UV absorption spectrum measurement and the fluorescence spectrum measurement involved a sample with a DNA strand concentration of 0.4 µM, 50 mM (pH7.0) of a phosphoric acid buffer, and 100 mM of NaCl. Further, complementary strand 5'-d(AAAAAAAAAAAAA)-3' (SEQ ID NO:2) for the DNA probe was added to the sample to achieve 0 µM (that is, only the DNA probe; the result being indicated by the symbol a in the drawings) or 0.4 µM (the result being indicated by the symbol b in the drawings). The fluorescence spectrum measurement used light of 488 nm (with a width of 1.5 nm) as excitation light.

Figure 2:
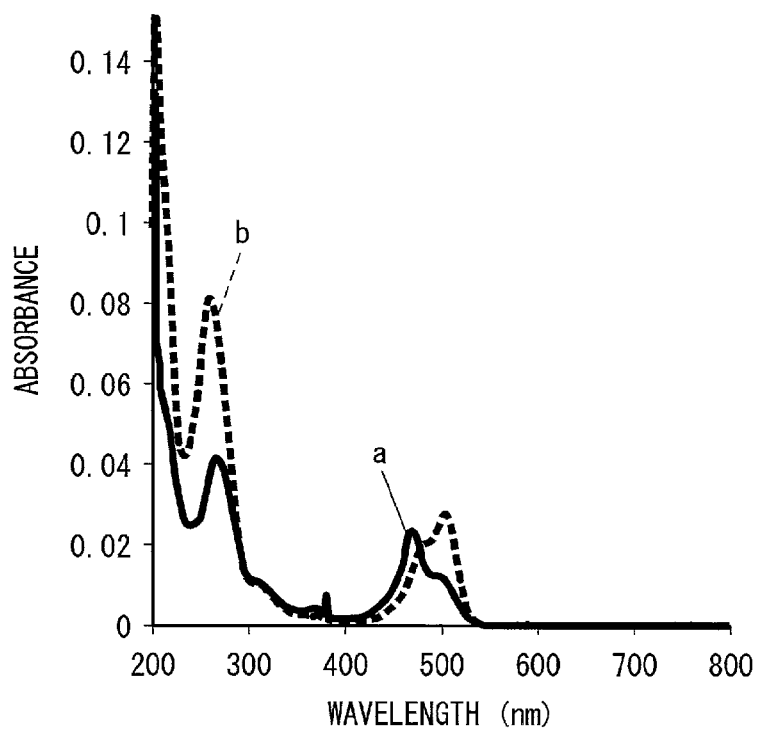
FIG. 2 is a view showing a UV absorption spectrum of a DNA probe in accordance with an example of the present invention.
Figure 3:
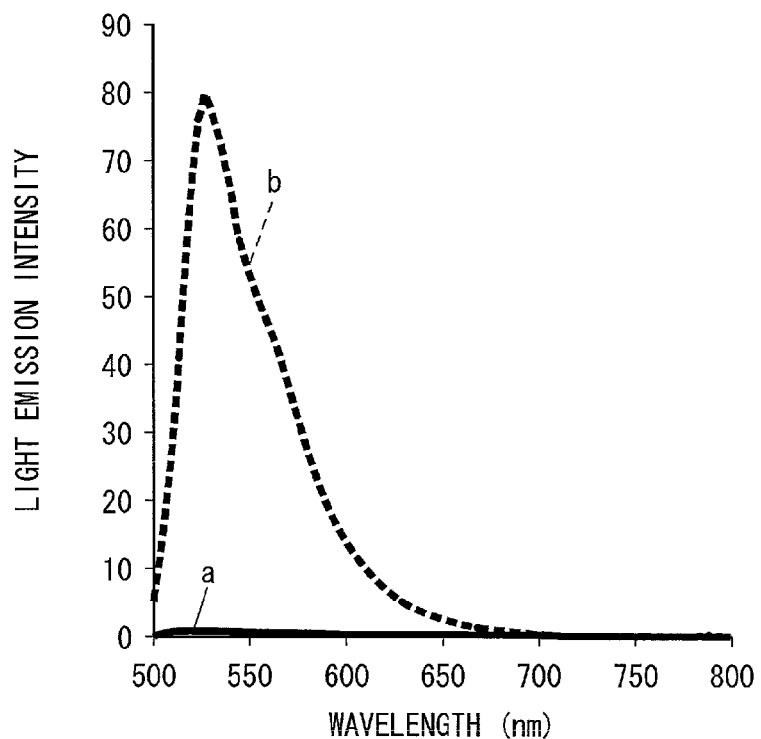
FIG. 3 is a view showing a fluorescence spectrum of a DNA probe in accordance with an example of the present invention.

FIGS. 2 and 3 show the results of the above measurements. FIG. 2 is a graph illustrating a UV absorption spectrum of a DNA probe in accordance with an example of the present invention. FIG. 3 is a graph illustrating a fluorescence spectrum of a DNA probe in accordance with an example of the present invention.

FIGS. 2 and 3 show that bond of the DNA probe with a complementary strand DNA causes emission of fluorescence. Therefore, the DNA probe of this Example had a clear fluorescence emission switching function.

Example 5

This Example synthesized DNA probe 5'-d(TACCAGNCACCAT)-3' (SEQ ID NO:3) (where N is a nucleoside containing a fluorescence dye) and then purified the DNA probe by a method similar to that of Example 3 under conditions similar to those of Example 3. Next, this Example performed a UV absorption spectrum measurement and a fluorescence spectrum measurement for the above DNA probe by a method similar to that of Example 4 under conditions similar to those of Example 4.

Figure 4:
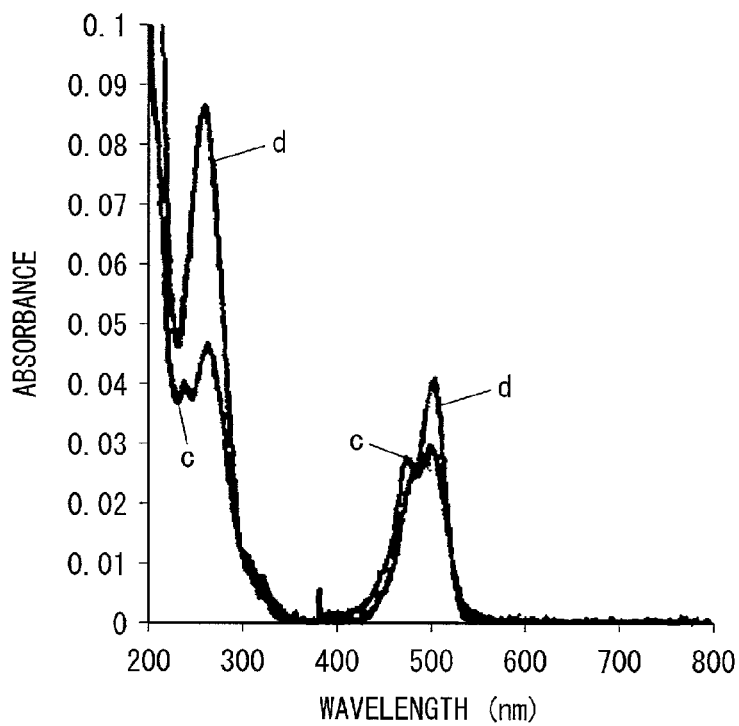
FIG. 4 is a view showing a UV absorption spectrum of a DNA probe in accordance with another example of the present invention.
Figure 5:
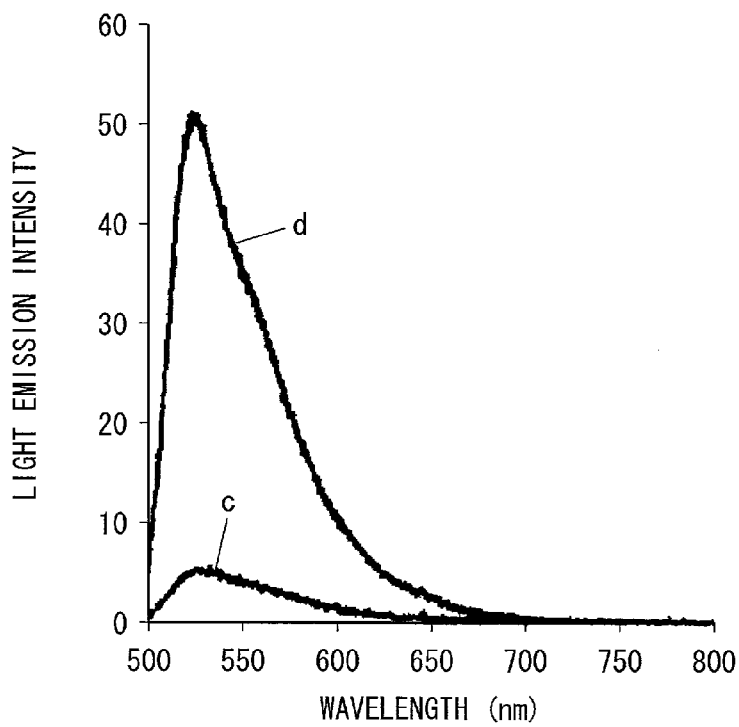
FIG. 5 is a view showing a fluorescence spectrum of a DNA probe in accordance with another example of the present invention.

FIGS. 4 and 5 show the results of the above measurements. FIG. 4 is a graph illustrating a UV absorption spectrum of a DNA probe in accordance with another example of the present invention. FIG. 5 is a graph illustrating a fluorescence spectrum of a DNA probe in accordance with another example of the present invention. FIGS. 4 and 5 each show (i) the symbol c to indicate a result obtained in the case where no complementary strand for the DNA probe was added to the sample and (ii) the symbol d to indicate a result obtained in the case where a complementary strand was added.

FIGS. 4 and 5 show that bond of the DNA probe with a complementary strand DNA causes emission of fluorescence. Therefore, the DNA probe of this Example had a clear fluorescence emission switching function.

Example 6

Synthesis of DMTr Form of Nucleoside Containing Fluorescence Dye

This Example synthesized, by the following reaction formulae (H) to (J), a DMTr form of a nucleoside containing a fluorescence dye, the DMTr form being represented by the following formula (32). Specifically, this Example first synthesized (i) a DMTr form of an NHS activator of a nucleoside and (ii) a fluorescence dye, and then synthesized a DMTr form of a nucleoside containing a fluorescence dye. The description below deals with a specific method used.

[Chem. 30]

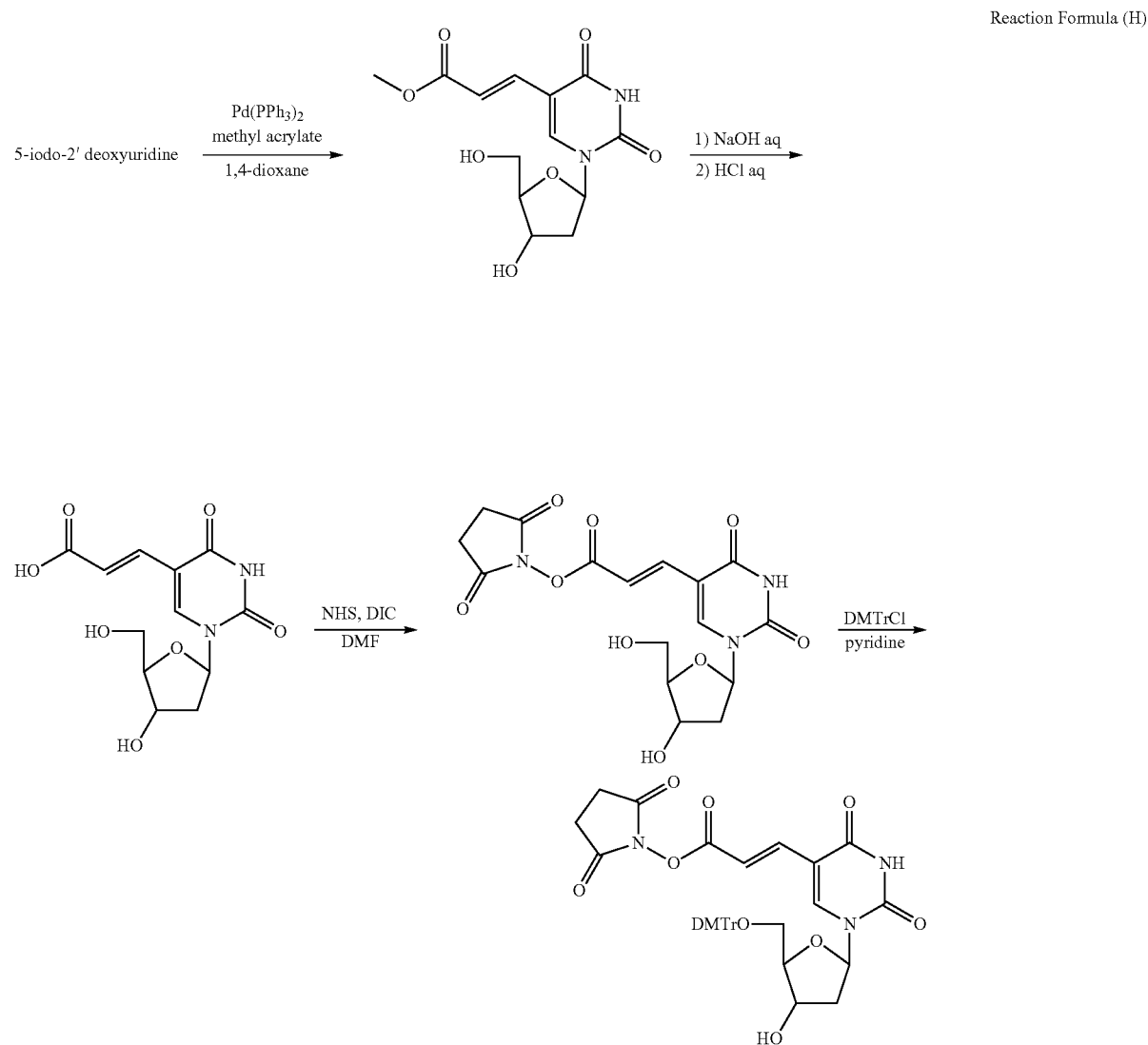

Reaction Formula (H)

-continued
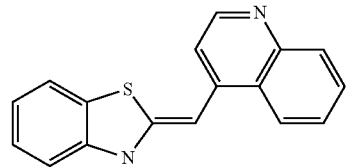
Reaction Formula (I)
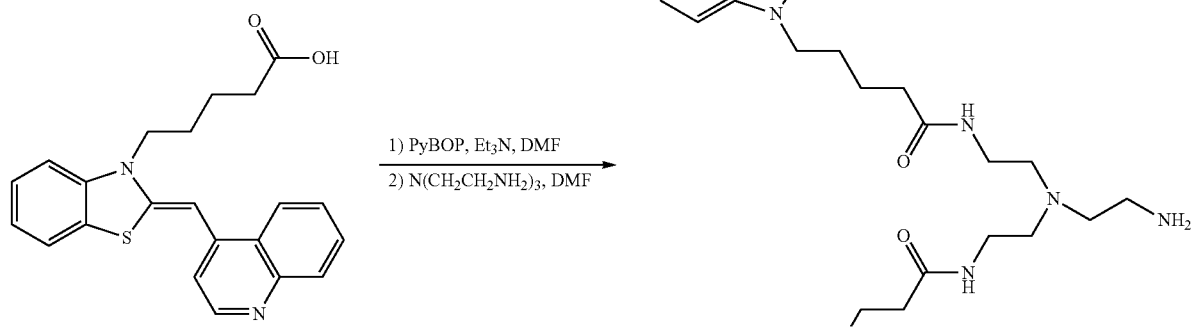
Reaction Formula (J)
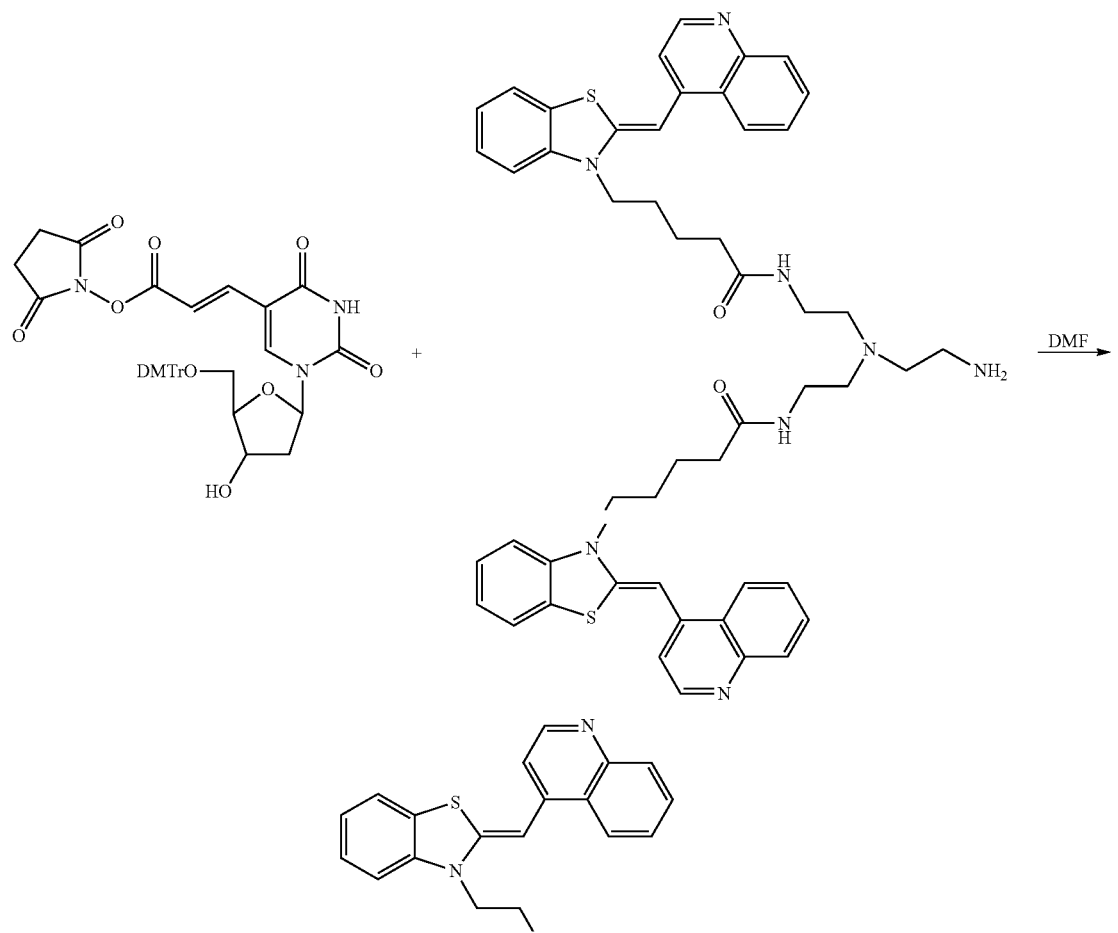

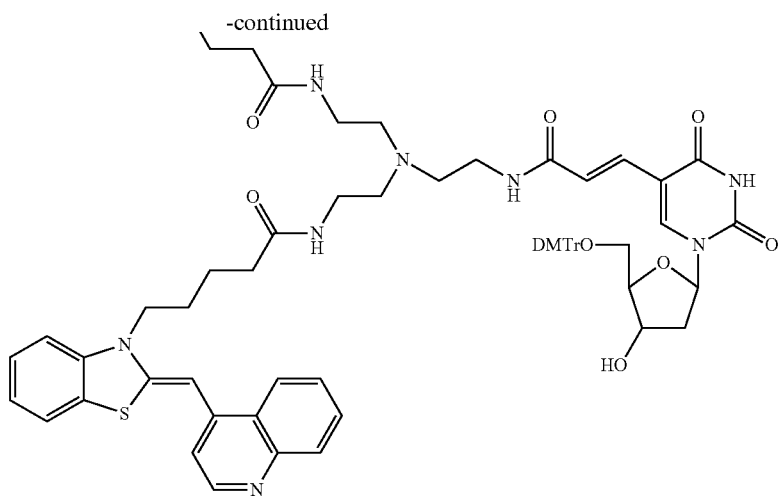

6-1: Synthesis of 5'-O-DMTr 5-(2-succinimidoxy-carbonyl-(E)-vinyl)-2'-deoxyuridine First, an NHS activator of a nucleoside was synthesized. DMF (60 ml) was added to (i) (E)-5-(2-carboxyvinyl)-2'-deoxyuridine (10 g, FW 298.25), (ii) N-hydroxy succinimide (7.7 g, FW 115.09), and (iii) N,N-diisopropyl carbodiimide (8.5 g, FW 126.20), and the resulting mixture was stirred at 25° C. for 4 hours. Then, an acetic acid (93.8 ml) was added, and the resulting mixture was dropped into a mixed solution of dichloromethane (300 ml) and water (300 ml) while the mixed solution was being stirred vigorously. A precipitate produced thereby was filtered, washed with ultrapure water, and dried.

Next, a DMTr form of an NHS activator of a nucleoside was synthesized, the DMTr form being represented by the following formula (30):

[Chem. 31]

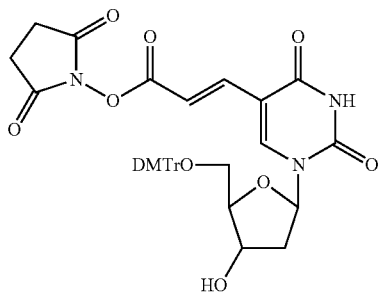
(30)

Then, pyridine (20 ml) was added to (i) a precipitate (2 g, FW 395.32) produced thereby and (ii) DMTrCl (1.9 g, FW 228.83), and the resulting mixture was stirred at 25° C. overnight. After that, a sodium chloride aqueous solution was added, and the mixture was extracted with use of ethyl acetate. An organic layer was washed with a saturated saline, and dried with use of magnesium sulfate. Next, a solvent was evaporated by evaporation, and the remaining was separated with use of a silica gel column (2-10% MeOH, 1% Et$_3$N/CH$_2$Cl$_2$). From a fraction containing a target compound, the solvent was evaporated off. The remaining was dissolved in a small amount of dichloromethane, to which hexane was added. Then, a resulting precipitate was filtered, washed with hexane, and dried. This produced 1.6 g of the target compound (FW 697.69, yield: 46%) as white powder. The following shows measurement data for the target compound.

$^1$H-NMR (CD$_3$OD): 8.07 (s, 1H), 7.40 (d, J=7.3 Hz, 2H), 7.28 (m, 6H), 7.20 (d, J=7.3 Hz, 1H), 7.11 (d, J=15.9 Hz, 1H), 6.97 (d, J=15.7 Hz, 1H), 6.85 (m, 4H), 6.21 (t, J=6.5 Hz, 1H), 4.46 (q, J=3.1 Hz, 1H), 4.11 (dd, J=6.6, 3.4 Hz, 1H), 3.76 (s, 3H), 3.75 (s, 3H), 3.66 (s, 2H), 3.37 (s, 2H), 2.65 (d, J=8.8 Hz, 1H), 2.54 (t, J=6.8 Hz, 1H), 2.45 (ddd, J=13.8, 6.3, 3.2 Hz, 1H), 2.38 ppm (q, J=6.8 Hz, 1H)

$^{13}$C-NMR (CD$_3$OD): 174.4, 171.9, 166.8, 163.4, 160.23, 160.21, 150.9, 145.9, 145.5, 136.9, 136.6, 131.3, 131.2, 129.2, 128.9, 128.1, 114.27, 114.25, 110.0, 88.37, 88.06, 72.71, 64.96, 55.77, 52.29, 47.73, 42.03, 29.84, 28.36, 26.50, 9.37 ppm

6-2: Synthesis of N,N-bis({[3-(4-valeryl)benzoxazol-2-ylidene]methyl}quioline))-2-amidoethyl)ethylamine Next, a fluorescence dye represented by the following formula (31) was synthesized.

[Chem. 32]
(31)

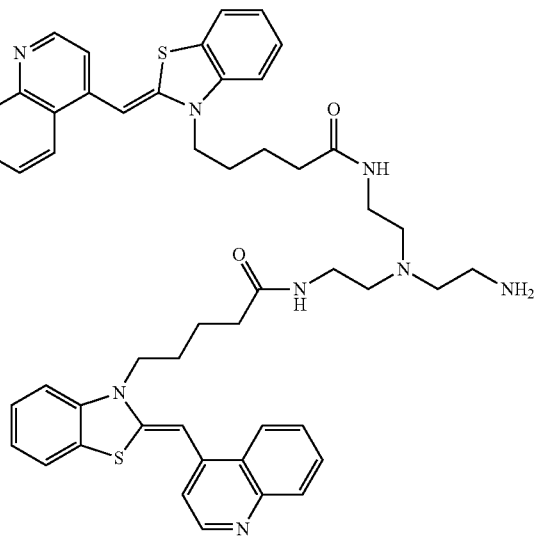

First, DMF (10 ml) was added to (i) 4-{[3-(4-Carboxybutyl) benzoxazol-2-ylidene]methyl}quinoline (1.9 g, FW 376.47) and (ii) PyBOP (5.2 g, FW 520.39), and the resulting mixture was stirred at 25° C. for 30 minutes. The reaction solution was dropped into a DMF (10 ml) solution of tris(2-aminoethyl)amine (314 mg, FW 146.23), and the resulting mixture was stirred at 25° C. overnight. A solvent was evaporated by evaporation, and separated with use of a silica gel column (7-20% MeOH, 1% Et$_3$N/CH$_2$Cl$_2$). A solvent of a fraction containing a target compound was evaporated by evaporation. The remaining was dissolved in a small amount of methanol, to which diethyl ether was added. Then, a precipitate was filtered and dried. This produced 593 mg of the target compound (FW 863.15, yield: 28%) as orange-colored powder. The following shows measurement data for the target compound.

$^1$H-NMR (DMSO-d$_6$): 8.72 (d, J=5.1 Hz, 2H), 8.35 (d, J=7.8 Hz, 2H), 7.92 (dd, J=8.3, 1.2 Hz, 2H), 7.84 (t, J=5.8 Hz, 2H), 7.69 (m, 2H), 7.61 (dd, J=7.7, 1.1 Hz, 2H), 7.55 (m, 2H), 7.41 (d, J=4.9 Hz, 2H), 7.30 (m, 2H), 7.20 (d, J=8.3 Hz, 2H), 7.03 (td, J=7.6, 0.90 Hz, 2H), 6.44 (s, 2H), 4.17 (t, J=6.6 Hz, 4H), 3.05 (dd, J=12.5, 6.6 Hz, 4H), 2.73 (t, J=5.5 Hz, 2H), 2.38 (t, J=6.5 Hz, 4H), 2.17 (t, J=6.6 Hz, 4H), 1.70 ppm (m, 8H)

$^{13}$C-NMR (DMSO-d$_6$): 172.1, 149.7, 148.5, 148.1, 142.5, 141.2, 129.3, 129.0, 126.9, 125.4, 125.3, 123.9, 122.4, 121.9, 121.4, 113.2, 109.5, 84.4, 54.9, 53.6, 43.9, 37.0, 36.7, 35.0, 25.5, 22.7, 7.4 ppm HRMS (ESI+) calcd for C$_{50}$H$_{54}$N$_8$O$_2$S$_2$ ([M+H]$^+$) 863.39, found 863.3907.

6-3: Synthesis of 5'O-DMTr-5-(2-[2-{N,N-bis({[3-(4-valeryl)benzoxazol-2-ylidene]methyl}quioline)-2-amidoethyl) Aminoethyl]carbomoyl-(E)-vinyl)-2-deoxyuridine Next, a DMTr form of a nucleoside containing a fluorescence dye was synthesized, the DMTr form being represented by the following formula (32):

[Chem. 33]

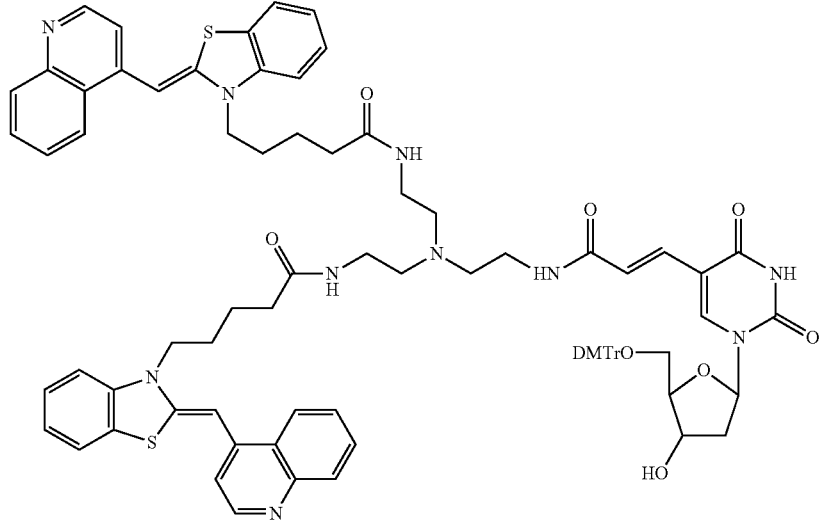

(32)

First, DMF (10 ml) was added to (i) 5'-O-DMTr 5-(2-succinimidoxycarbonyl-(E)-vinyl)-2'-deoxyuridine (500 mg, FW 697.69) and (ii) N,N-bis({[3-(4-valeryl) benzoxazol-2-ylidene]methyl}quioline))-2-amidoethyl)ethylamine (621 mg, FW 863.15), and the resulting mixture was stirred at 25° C. for 2 hours. Then, DMAP (8.8 mg, FW 122.17) was added to the reaction solution, which was then stirred at 25° C. overnight. A solvent was evaporated by evaporation, and separated with use of a silica gel column (7-15% MeOH, 1% $Et_3N/CH_2Cl_2$). The remaining was dissolved in a small amount of methanol, to which diethyl ether was added. Then, a precipitate was filtered and dried. The resulting powder was washed with water, filtered, and dried. This produced 256 mg of a target compound (FW 1445.75, yield: 25%) as orange-colored powder. The following shows measurement data for the target compound.

$^1$H-NMR (DMSO-$d_6$): 8.57 (d, J=6.1 Hz, 2H), 8.48 (d, J=8.3 Hz, 2H), 7.81 (m, 9H), 7.58 (t, J=7.5 Hz, 2H), 7.45-7.15 (m, 16H), 7.08 (s, 2H), 6.85 (dd, J=8.9, 6.0 Hz, 4H), 6.64 (s, 2H), 6.11 (t, J=6.6 Hz, 1H), 5.28 (s, 1H), 4.35 (m, 4H), 4.20 (m, 1H), 3.87 (dd, J=9.5, 4.2 Hz, 1H), 3.69 (s, 3H), 6.68 (s, 3H), 3.19-3.06 (m, 10H), 2.44 (m, 4H), 2.26 (qui, J=6.7 Hz, 2H), 2.17 (t, J=6.5 Hz, 4H), 1.71 ppm (m, 8H)

$^{13}$C-NMR (DMSO-$d_6$): 172.0, 165.7, 161.7, 158.0, 154.4, 149.2, 146.3, 144.8, 143.9, 142.7, 141.5, 140.4, 135.55, 135.46, 132.3, 131.1, 129.6, 127.8, 127.6, 127.5, 126.6, 126.2, 124.4, 123.9, 123.8, 123.1, 123.0, 122.4, 121.8, 113.2, 111.3, 110.1, 109.3, 86.0, 85.6, 84.7, 70.2, 63.9, 55.0, 54.9, 53.4, 53.2, 44.8, 34.8, 25.9, 22.5 ppm HRMS (ESI+) calcd for $C_{83}H_{85}N_{10}O_{10}S_2$ ($[M+H]^+$) 1445.59, found 1445.59301.

Using the above method makes it possible to achieve higher synthesizing efficiency. A DMTr form of a nucleoside containing a fluorescence dye, the DMTr form having been synthesized by the above method, can be used to produce a dye-containing phosphoramidite compound by producing an amidite form from the DMTr form by the method described in 2-3 of Example 2.

INDUSTRIAL APPLICABILITY

The present invention facilitates producing a nucleic acid containing a dye exhibiting an exciton effect, and can thus be used suitably for, (i) e.g., a primer, a probe capable of detecting a detection target effectively, and a labeling substance and (ii) production thereof. The present invention can therefore be used suitably for (i) a nucleic acid for a wide variety of applications such as research, clinical activity, diagnosis, detection of genes in vitro, and detection of genes in vivo and (ii) production of the nucleic acid.

The invention claimed is:

1. A compound, which is represented by one of the following formula (1), or (2)

[Chem. 1]

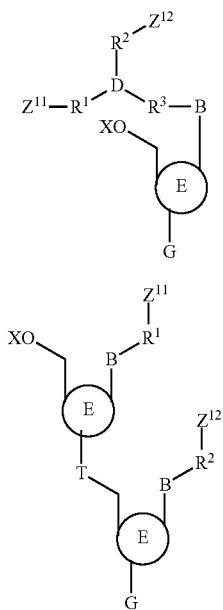

where, in the above formulae (1), and (2)

G is a phosphoramidite group represented by the following formula (33) or a hydroxyl group,

[Chem. 2]

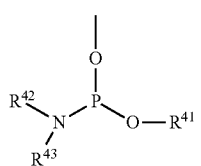

$R^{41}$ is a protecting group of a phosphite group, $R^{42}$ and $R^{43}$ are independently alkyl groups or aryl groups, B is a natural nucleic acid base moiety (9-adeninyl, 9-guaninyl, 1-cytosinyl, 1-thyminyl, or 1-uracilyl) or an artificial nucleic acid base moiety, E is a 2-deoxy-1-ribosyl moiety or a 1-ribosyl moiety, X is a hydrogen atom, dimethoxytrityl group, a phosphate group, a diphosphate group, or a triphosphate group, $R^1$ and $R^2$ are independently linkers each having a main chain, and an atom forming the main chain optionally has a substituent, $R^3$ is a linker having a main chain, or is absent, and an atom forming the main chain optionally has a substituent, D is $CR^{11}$, N, P, P=O, B (boron atom), $SiR^{11}$, or absent, and $R^{11}$ is a hydrogen atom or an alkyl group for $CR^{11}$ and is an alkyl group for $SiR^{11}$, D is directly attached to B in a case where $R^3$ does not exist and D exists, $R^1$ and $R^2$ are directly attached to $R^3$ in a case where $R^3$ exists and D does not exist, and $R^1$ and $R^2$ are directly attached to B in a case where both $R^3$ and D do not exist, T is phosphate bridge, and wherein, in the phosphate bridge, one or more oxygen atoms are optionally substituted for by one or more sulfur atoms, $Z^{11}$ and $Z^{12}$ are independently uncharged fluorescent dye-derived substituent moieties each having a fluorescent property and exhibiting an exciton effect, and are independently represented by the following formula (12), (28), or (29),

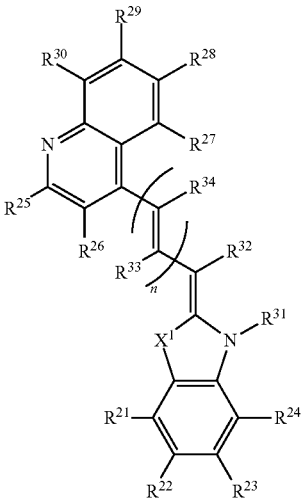

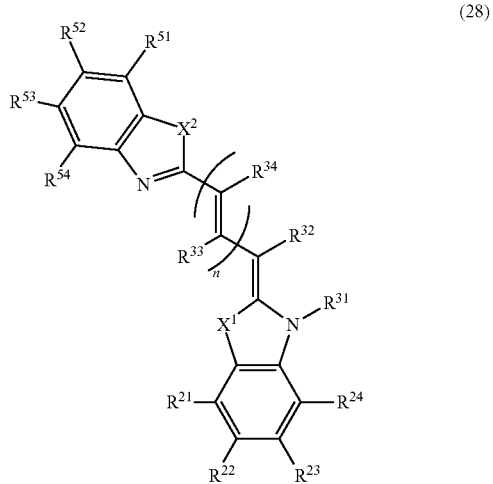

-continued (29)

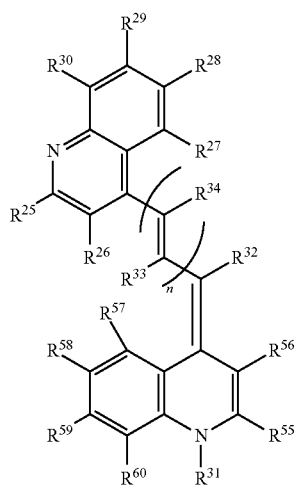

where, in the above formulae (12), (28), and (29), $X^1$ and $X^2$ are independently O, S, Se, or Te, n is zero or a positive integer of 5 or less, $R^{21}$ to $R^{30}$, $R^{32}$ to $R^{34}$, $R^{51}$ to $R^{60}$ are independently a hydrogen atom, a halogen, a lower alkyl group, a lower alkoxy group, a nitro group, or an amino group, and $R^{28}$ and $R^{29}$ are optionally attached to each other, and $R^{58}$ and $R^{59}$ are optionally attached to each other, $R^{31}$ is a linking group which is attached to $R^1$ or $R^2$ in the above formula (1), or (2), and in a case where n is an integer of 2 or more, $R^{33}$ moieties may be identical to or different from each other, and $R^{34}$ moieties may be identical to or different from each other, and in the above formula (1), a chemical structure represented by the following formula (1a) being a chemical structure represented by the following formula (4) or (5); and in the above formula (2), a chemical structure represented by the following formula (2a) being a chemical structure represented by the following formula (6) or (7),

[Chem. 3]

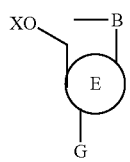

(1a)

[Chem. 4]

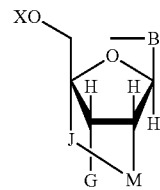

(5)

(2a)

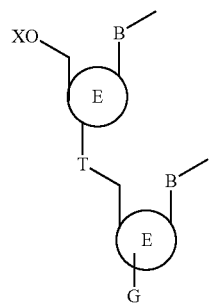

(6)

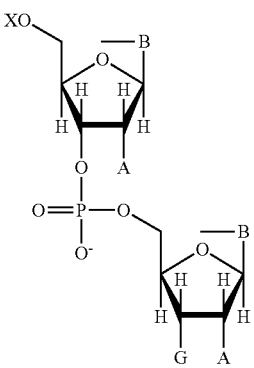

(7)

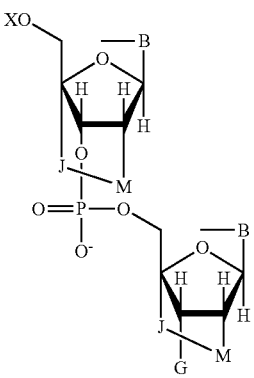

where, in the above formulae (4) through (7),

A is a hydrogen atom, a hydroxyl group, an alkyl group, or an electron attracting group, and M and J are independently $CH_2$, NH, O, or S provided that J cannot be NH.

2. The compound as set forth in claim 1, wherein main chains of $R^1$, $R^2$, and $R^3$ are independently constituted by two or more atoms.

3. The compound as set forth in claim 1, which is represented the following formula (8), (9), or (10)

[Chem. 5]

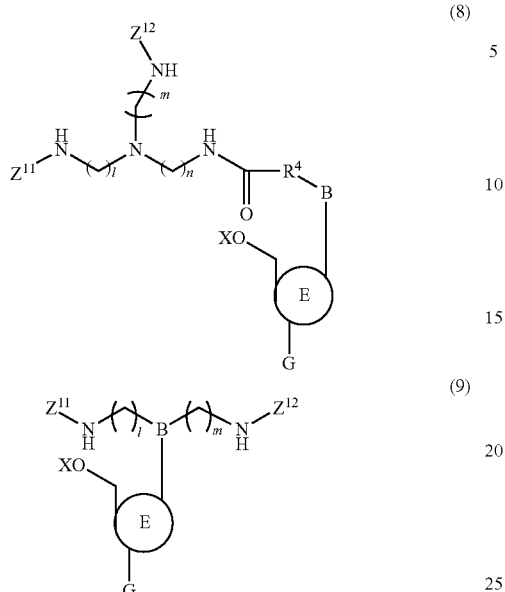

[Chem. 6]

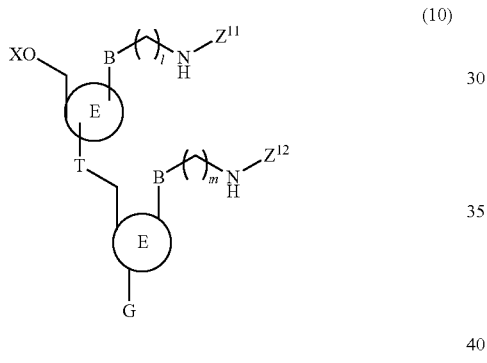

where, in the above formulae (8), (9), and (10),
l, m, and n are independently a positive integer, and
$R^4$ is a carbon-carbon single bond, a carbon-carbon double bond, a carbon-carbon triple bond, or absent.

4. The compound as set forth in claim 3,
wherein l, m, and n are 2, and $R^4$ is a carbon-carbon double bond.

5. The compound as set forth in claim 1, wherein:
$R^{31}$ is a C2-C100 polymethylene carbonyl group in the above formulae (12), (28), and (29); and
a carbonyl group portion of the C2-C100 polymethylene carbonyl group is attached to $R^1$ or $R^2$ in the above formula (1), or (2).

6. The compound as set forth in claim 1,
wherein $R^{41}$ is a cyanoethyl group, both $R^{42}$ and $R^{43}$ are an isopropyl group.

7. A kit for producing a nucleic acid, comprising a compound as recited in claim 1, and nucleotide(s) not substituted with a dye-derived substituent.

8. A method of producing a compound which is a compound as recited in claim 1 where G is a phosphoramidite group represented by the above formula (33),
the method comprising the step of reacting a phosphoramiditing reagent with a compound, which is recited in claim 1 where G is a hydroxyl group, in an aprotic solvent to produce the phosphoramidite analog of the compound.

9. A method of producing a nucleic acid, comprising:
carrying out a condensation reaction of a compound as recited in claim 1 and an oligonucleic acid by a phosphoramidite method, the compound as recited in claim 1 being such that G is a phosphoramidite group represented by the above formula (33).

10. A nucleic acid, comprising
a chemical structure, represented by one of the following formula (25), or (26), as a nucleotide portion,

[Chem. 8]

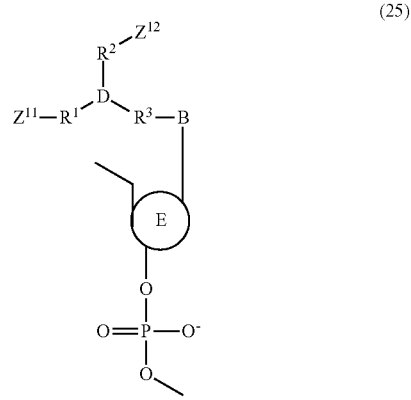

where, in the above formulae (25), and (26),
B is a natural nucleic acid base moiety (9-adeninyl, 9-guaninyl, 1-cytosinyl, 1-thyminyl, or 1-uracilyl) or an artificial nucleic acid base moiety,
E is a 2-deoxy-1-ribosyl moiety or a 1-ribosyl moiety,
$R^1$ and $R^2$ are independently linkers each having a main chain, and an atom forming the main chain optionally has a substituent,
$R^3$ is a linker having a main chain, or is absent, and an atom forming the main chain optionally has a substituent,
D is $CR^{11}$, N, P, P=O, B (boron atom), $SiR^{11}$, or absent, and $R^{11}$ is a hydrogen atom or an alkyl group for $CR^{11}$ and is an alkyl group for $SiR^{11}$,
D is directly attached to B in a case where $R^3$ does not exist and D exists, $R^1$ and $R^2$ are directly attached to $R^3$ in a case where $R^3$ exists and D does not exist, and $R^1$ and $R^2$ are directly attached to B in a case where both $R^3$ and D do not exist,
T is phosphate bridge, and wherein, in the phosphate bridge, one or more oxygen atoms are optionally substituted for by one or more sulfur atoms, $Z^{11}$ and $Z^{12}$ are independently uncharged fluorescent dye-derived substituent moieties each having a fluorescent property and exhibiting an exciton effect, and are independently represented by the following formula (12), (28), or (29), (12)

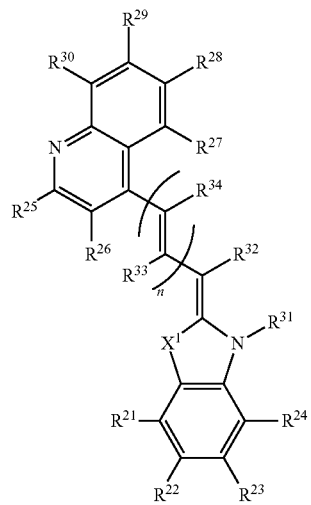

(28)

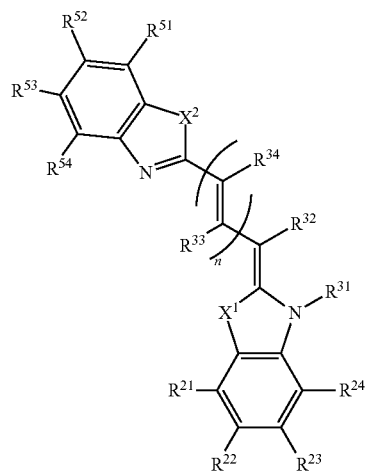

(29)

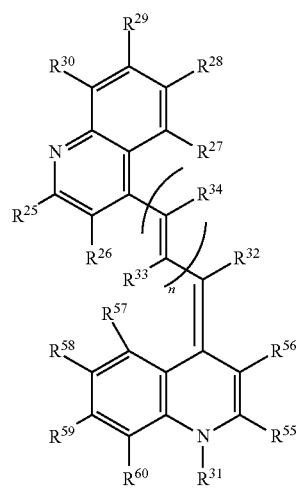

where, in the above formulae (12), (28), and (29), $X^1$ and $X^2$ are independently O, S, Se, or Te, n is zero or a positive integer of 5 or less, $R^{21}$ to $R^{30}$, $R^{32}$ to $R^{34}$, $R^{51}$ to $R^{60}$ are independently a hydrogen atom, a halogen, a lower alkyl group, a lower alkoxy group, a nitro group, or an amino group, and $R^{28}$ and $R^{29}$ are optionally attached to each other, and $R^{58}$ and $R^{59}$ are optionally attached to each other, $R^{31}$ is a linking group which is attached to $R^1$ or $R^2$ in the above formula (25), or (26), and in a case where n is an integer of 2 or more, $R^{33}$ moieties may be identical to or different from each other, and $R^{34}$ moieties may be identical to or different from each other, and in the above formula (25), a chemical structure represented by the following formula (1a') being a chemical structure represented by the following formula (4') or (5'); and in the above formula (26), a chemical structure represented by the following formula (2a') being a chemical structure represented by the following formula (6') or (7'), (1a')

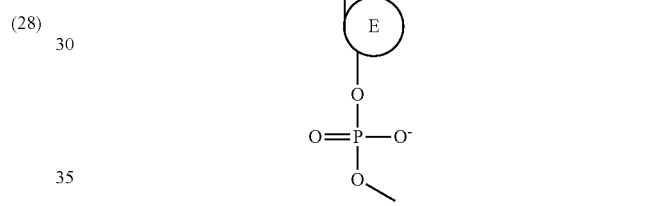

(4')

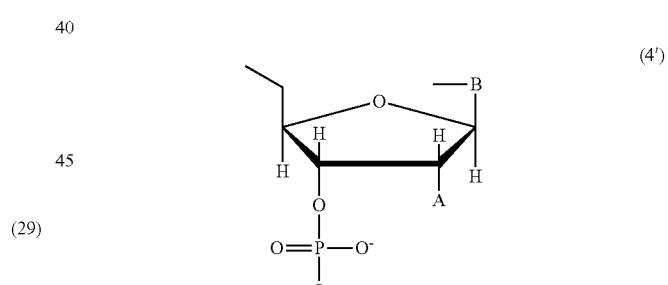

(5')

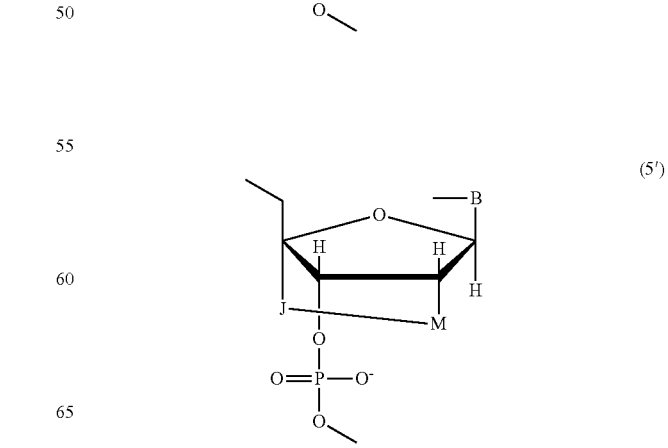

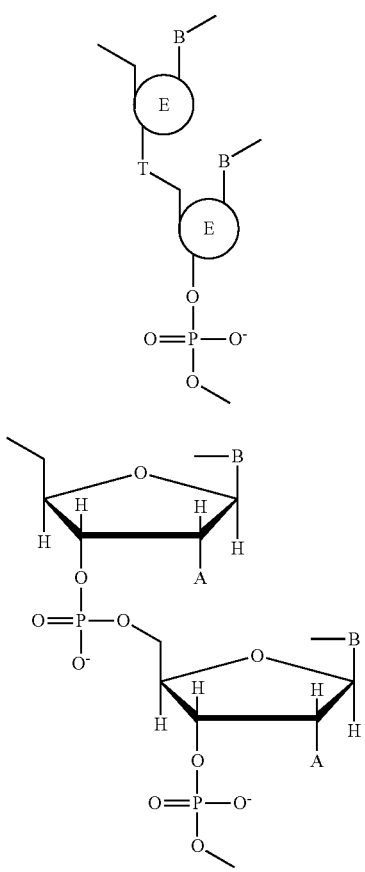
where, in the above formulae (4') through (7'),
A is a hydrogen atom, a hydroxyl group, an alkyl group, or an electron attracting group, and
M and J are independently $CH_2$, NH, O, or S provided that J cannot be NH.
11. The nucleic acid as set forth in claim 10, which is produced by the method as recited in claim 9.
* * * * *